United States Patent
Alabdulrahman et al.

(10) Patent No.: US 8,541,477 B2
(45) Date of Patent: Sep. 24, 2013

(54) METHODS OF DEPOLYMERIZING TEREPHTHALATE POLYESTERS

(75) Inventors: Abdullah M Alabdulrahman, Riyadh (SA); Hamid A Almegren, Riyadh (SA); Fares D Alsewailem, Riyadh (SA); Phillip Joe Brock, Sunnyvale, CA (US); Daniel Joseph Coady, San Jose, CA (US); Kazuki Fukushima, San Jose, CA (US); James Lupton Hedrick, Pleasanton, CA (US); Hans Werner Horn, San Jose, CA (US); Julia Elizabeth Rice, Sunnyvale, CA (US)

(73) Assignees: International Business Machines Corporation, Armonk, NY (US); King Abdulaziz City for Science and Technology, Riyadh (SA)

( * ) Notice: Subject to any disclaimer, the term of this patent is extended or adjusted under 35 U.S.C. 154(b) by 279 days.

(21) Appl. No.: 13/040,550

(22) Filed: Mar. 4, 2011

(65) Prior Publication Data

US 2012/0223270 A1    Sep. 6, 2012

(51) Int. Cl.
*C08J 11/04*    (2006.01)

(52) U.S. Cl.
USPC ........... 521/48.5; 521/40; 521/48; 528/308.1; 528/480; 528/495; 502/167; 502/200; 564/225

(58) Field of Classification Search
USPC ................ 521/40, 40.5, 48, 48.5; 528/308.1, 528/480, 491, 495; 564/1, 225, 226, 227, 564/228, 229, 243; 502/100, 150, 162, 164, 502/167, 200; 548/300.1, 336.5, 337.1; 544/300.1, 336.5, 337.1
See application file for complete search history.

(56) References Cited

U.S. PATENT DOCUMENTS

| | | | |
|---|---|---|---|
| 3,254,054 A | 5/1966 | Boerma et al. |
| 4,002,667 A | 1/1977 | Thompson |
| 4,293,456 A | 10/1981 | Reischl |
| 4,652,667 A | 3/1987 | Green |
| 4,663,472 A | 5/1987 | Green |
| 4,681,967 A | 7/1987 | Green |

(Continued)

FOREIGN PATENT DOCUMENTS

| | | |
|---|---|---|
| CA | 2202941 A1 | 10/1998 |
| EP | 0723951 A1 | 7/1996 |

(Continued)

OTHER PUBLICATIONS

Kiesewetter et al, "Cyclic Guanidine Organic Catalysts: What is Magic About Triazabicyclodecene?" J.Org. Chem. 74(24), pp. 9490-9496 (2009).*

(Continued)

*Primary Examiner* — Frances Tischler
(74) *Attorney, Agent, or Firm* — Michael R. Roberts

(57) ABSTRACT

A method comprises forming a reaction mixture comprising a terephthalate polyester, a glycol comprising 2 to 5 carbons, and an amidine organocatalyst; and heating the reaction mixture at a temperature of about 120° C. or more to depolymerize the terephthalate polyester, thereby forming a terephthalate reaction product comprising a monomeric dihydroxy terephthalate diester; wherein the terephthalate reaction product contains terephthalate oligomers in an amount less than the amount of terephthalate oligomers that would result from i) substituting the amidine organocatalyst with an equimolar amount of a guanidine catalyst and ii) depolymerizing the terephthalate polyester under otherwise identical reaction conditions.

38 Claims, 12 Drawing Sheets

(56) References Cited

U.S. PATENT DOCUMENTS

| | | | |
|---|---|---|---|
| 6,090,913 | A | 7/2000 | Drauz et al. |
| 6,241,849 | B1 | 6/2001 | Franks |
| 6,262,294 | B1 | 7/2001 | Sako et al. |
| 6,720,448 | B2 | 4/2004 | Broccatelli |
| 6,911,546 | B2 * | 6/2005 | Hedrick et al. ............ 548/316.7 |
| 7,521,496 | B2 | 4/2009 | Tokuyasu et al. |
| 2004/0019234 | A1 | 1/2004 | Inada et al. |
| 2007/0299150 | A1 | 12/2007 | Nakao et al. |
| 2011/0004014 | A1 | 1/2011 | Hedrick et al. |

FOREIGN PATENT DOCUMENTS

| | | |
|---|---|---|
| JP | 11181072 A | 7/1999 |
| JP | 11302208 A | 11/1999 |
| JP | 2000169623 A | 6/2000 |
| JP | 2000219728 | 8/2000 |
| JP | 2001316327 A | 11/2001 |

OTHER PUBLICATIONS

Korean Intellectual Property Office, International Search Report (ISR) and Written Opinion (WO) for PCT/US2012/027364 filed Mar. 2, 2012, mailing date of ISR and WO was Sep. 25, 2012.

Bourissou, "Recent advances in the controlled preparation of poly(a-hydroxy acids): Metal-free catalysts and new monomers," Comptes Rendus Chimie 10 (2007) 775-794; Available online Jul. 13, 2007.

Kilinc, et al., "Recycling of Waste PET: Usage as Secondary Plasticizer for PVC," Polymer-Plastics Tech. and Eng. 44: 1379-1388, 2005.

Kim, et al., "Cure Kinetics of Biphenyl Epoxy Resin System Using Latent Catalysts," Journal of Applied Polymer Science, vol. 81, 2711-2720 (2001).

Kometani, et al., "The Evaluation of Metal and Tertiary Amine Catalyst in CASE Application," Proceeding of the Polyurethane Expo 2001, Sep. 30-Oct. 3, 2001.

Lohmeijer, et al., "Guanidine and Amidine Organocatalysts for Ring-Opening Polymerization of Cyclic Esters," Macromolecules 2006, 39, 8574-8583.

Nederberg, et al., "Organocatalytic Ring Opening Polymerization of Trimethylene Carbonate," Biomacromolecules 2007, 8, 153-160.

Pratt, et al., "Exploration, Optimization, and Application of Supramolecular Thiourea-Amine Catalysts for the Synthesis of Lactide (Co)polymers," Macromolecules 2006, 39, 7863-7871.

Shieh, et al., "Nucleophilic Catalysis with 1,8-Diazabicyclo[5.4.0]undec-7-ene (DBU) for the Esterification of Carboxylic Acids with Dimethyl Carbonate," J. Org. Chem. 2002, 67, 2188-2191.

Ying, et al., "Aza-Michael addition of aliphatic or aromatic amines to a,b-unsaturated compounds catalyzed by a DBU-derived ionic liquid under solvent-free conditions," Tetrahedron Letters 50 (2009) 1653-1657.

* cited by examiner

METHODS OF DEPOLYMERIZING TEREPHTHALATE POLYESTERS

BACKGROUND

The present invention relates to methods of depolymerizing terephthalate polyesters, and more specifically to methods of depolymerizing post-consumer poly(ethylene terephthalate) and/or poly(butylene terephthalate) for production of terephthalate diester monomers.

Recycling of plastic materials has an important role in the 21st century in reducing environmental pollution and saving petroleum resources. PET is an engineering thermoplastic widely used in clothing fibers, packaging films, food containers and beverage bottles, that contributes several billion pounds of waste to landfills every year. The recycling rate of PET bottles in the U.S. remains 27% as of 2008, lower than aluminum cans (48%). There are mainly two conventional methods of processing post-consumer PET, mechanical recycling and chemical recycling.

Mechanical recycling is the most commonly practiced, which entails melt-processing and remolding the post-consumer PET to form products other than beverage bottles due to the deterioration of the intrinsic viscosity of the PET during the melt process. Various additives and metal catalysts contained in PET bottles promote thermal degradation of the polyester chains. The thermal stability has been improved by utilizing a solid state polymerization process that employs catalysts in the post-consumer PET to increase and/or maintain the molecular weight high enough for the fabrication process (JP 2000-219728). However, there are practical concerns such as the color tone of the product when colored bottles are used as raw materials, and control over the polymerization rate of the post-consumer PET when using different amounts and types of catalysts.

Chemical recycling yields a high quality terephthalate starting material via the chemical breakdown of PET, but has the disadvantage of high energy consumption and overall higher processing cost compared to mechanical recycling. Energy consumption can be lowered with catalysts, such as zinc acetate, aluminum isopropoxide, sodium sulfate, NaOH, KOH, and zeolite, which have been reported to be effective catalysts for the depolymerization of post-consumer PET. However, some catalysts require pressurization and long reaction times. Another drawback is that many catalysts include a non-biodegradable metal in their chemical formulas, which can become a pollution factor unless recovered and reused.

Initiatives in the chemical recycling of PET are thus ideally focused on developing an environmentally safe, economically feasible, and industrially applicable process for widescale application. Chemical recycling methodologies that are energy efficient and do not involve heavy metals are highly desirable even though the catalysts are usually not contained in the purified monomers.

SUMMARY

Accordingly, in an embodiment, a method is disclosed comprising:

forming a reaction mixture comprising a terephthalate polyester, a glycol comprising 2 to 5 carbons, and an amidine organocatalyst; and heating the reaction mixture at a temperature of about 120° C. or more to depolymerize the terephthalate polyester, thereby forming a terephthalate reaction product comprising a monomeric dihydroxy terephthalate diester;

wherein the terephthalate reaction product contains terephthalate oligomers in an amount less than the amount of terephthalate oligomers that would result from i) substituting the amidine organocatalyst with an equimolar amount of a guanidine catalyst and ii) depolymerizing the terephthalate polyester under otherwise identical reaction conditions.

Another method is disclosed comprising:

forming a reaction mixture comprising a terephthalate polyester, an amidine organocatalyst, and a glycol in an amount of about 4 to about 20 molar equivalents relative to a terephthalate repeat unit, the glycol comprising 2 to 5 carbons, wherein the glycol is a co-catalyst; and heating the reaction mixture at a temperature in the range of about 120° C. to about 210° C. to depolymerize the terephthalate polyester, thereby forming a terephthalate reaction product comprising a monomeric dihydroxy terephthalate diester.

Also disclosed is a method of preparing bis(2-hydroxyethyl)terephthalate (BHET), comprising:

forming a reaction mixture comprising poly(ethylene terephthalate) (PET), ethylene glycol in an amount of 4 to about 20 molar equivalents relative to a PET repeat unit, and an amidine organocatalyst; and heating the reaction mixture at a temperature in the range of about 120° C. to about 210° C. to depolymerize the poly(ethylene terephthalate), thereby producing a terephthalate reaction product comprising bis(2-hydroxyethyl)terephthalate (BHET).

Further disclosed is a method of preparing bis(4-hydroxybutyl)terephthalate (BHBT), comprising:

forming a reaction mixture comprising poly(butylene terephthalate) (PBT), an amidine organocatalyst, and 4 to 20 molar equivalents of 1,4-butanediol relative to moles of poly(butylene terephthalate) repeat unit present in the PBT; and heating the reaction mixture at a temperature in the range of about 120° C. to about 210° C. to depolymerize the poly(butylene terephthalate), thereby forming a terephthalate reaction product comprising bis(4-hydroxybutyl)terephthalate (BHBT).

The above-described and other features and advantages of the present invention will be appreciated and understood by those skilled in the art from the following detailed description, drawings, and appended claims.

Figure 5:
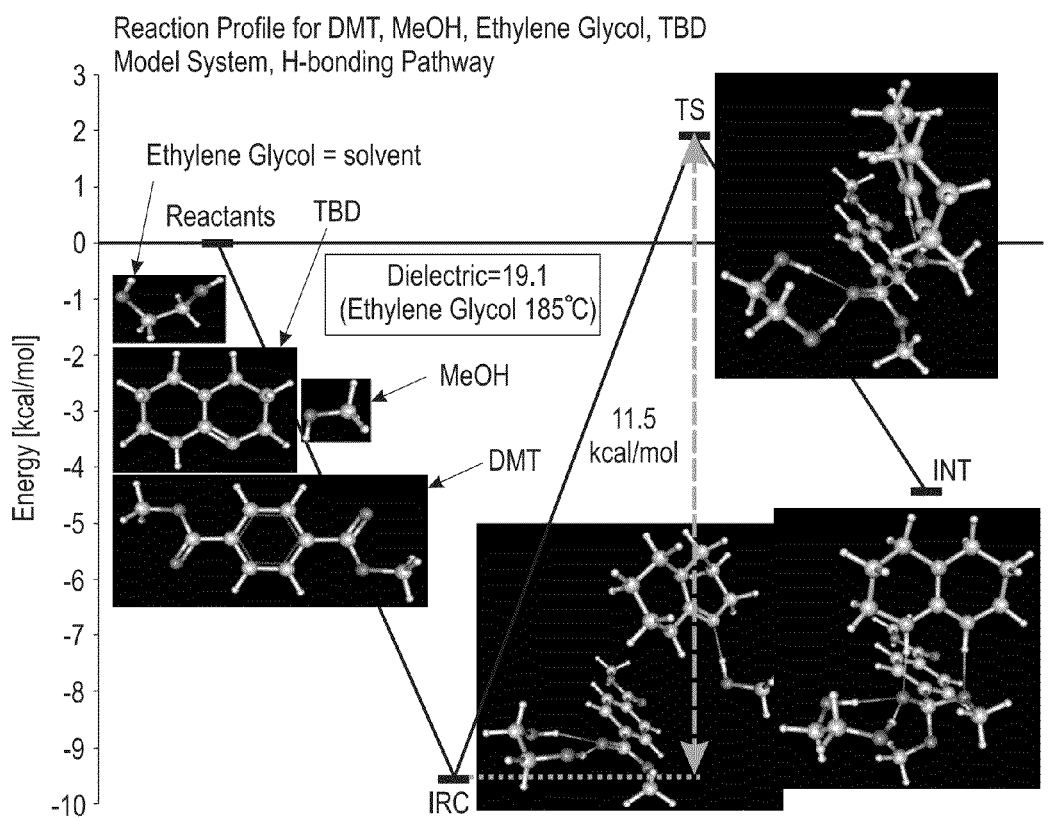

FIG. 5 is a reaction profile showing calculated energies of various transition state complexes in the methanolysis of dimethyl terephthalate (DMT) when catalyzed by TBD and EG.

Figure 6:
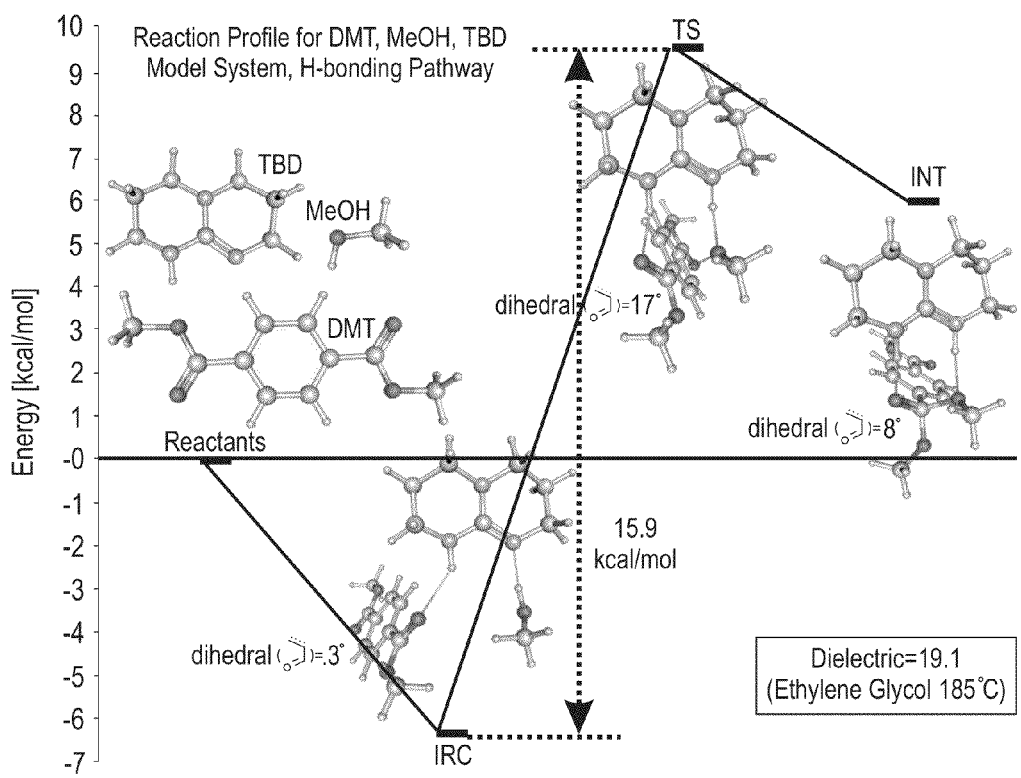

FIG. 6 is a reaction profile showing calculated energies of various transition state complexes in the methanolysis of dimethyl terephthalate (DMT) catalyzed by TBD.

Figure 7:
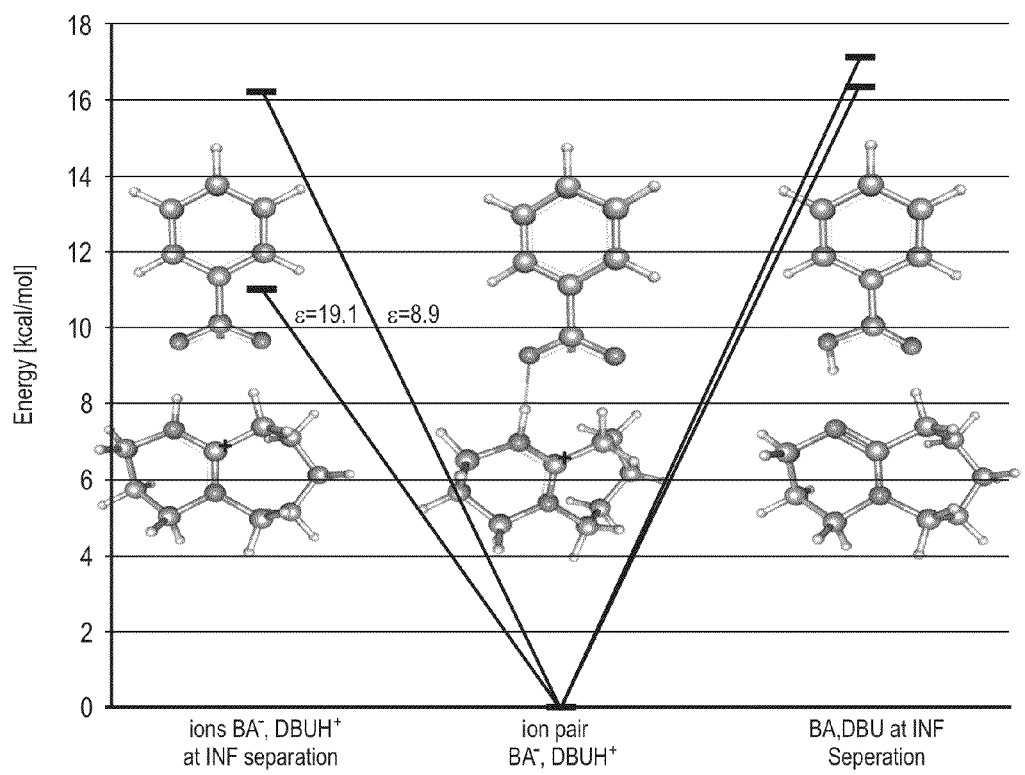

FIG. 7 is an energy diagram of the dissociation behavior of DBU/BA system at a solvent dielectric epsilon=19.1 (EG at 185° C.) and at epsilon=8.9 (CH$_2$Cl$_2$ at 25° C.).

Figure 8:
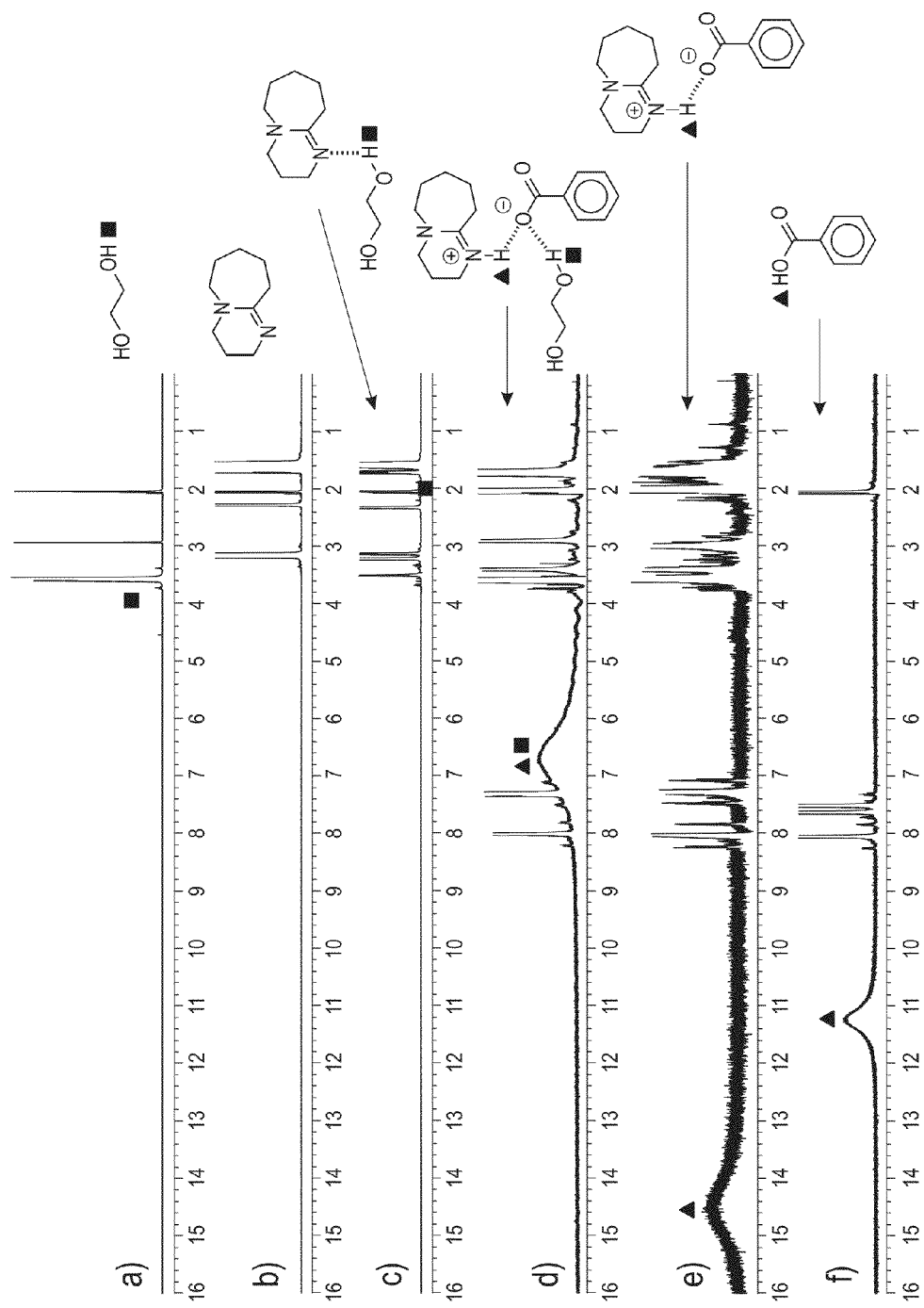

FIG. 8 is a set of 400 MHz $^1$H NMR spectra of a) EG, b) DBU, c) DBU+EG (1:1), d) DBU-BA+EG (1:1), e) DBU-BA, f) BA in acetone-d6 (0.1 mmol/mL).

Figure 9:
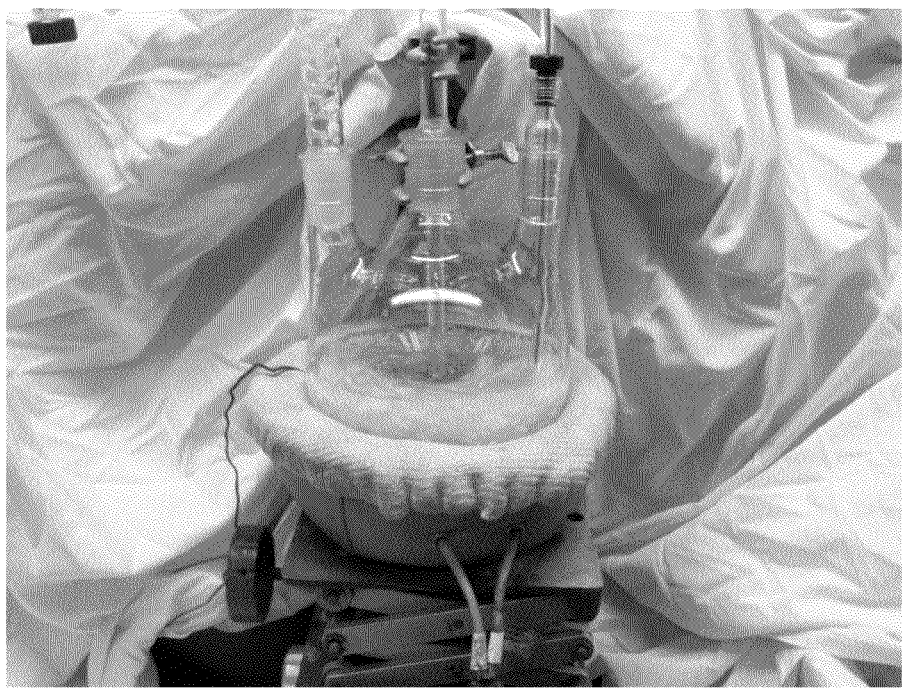

FIG. 9 is a photograph of a reaction setup of Example 26. The vessel contains the reactants before the depolymerization. The reaction mixture contains undissolved PET. This is a scaled up depolymerization relative to the other examples.

Figure 10:
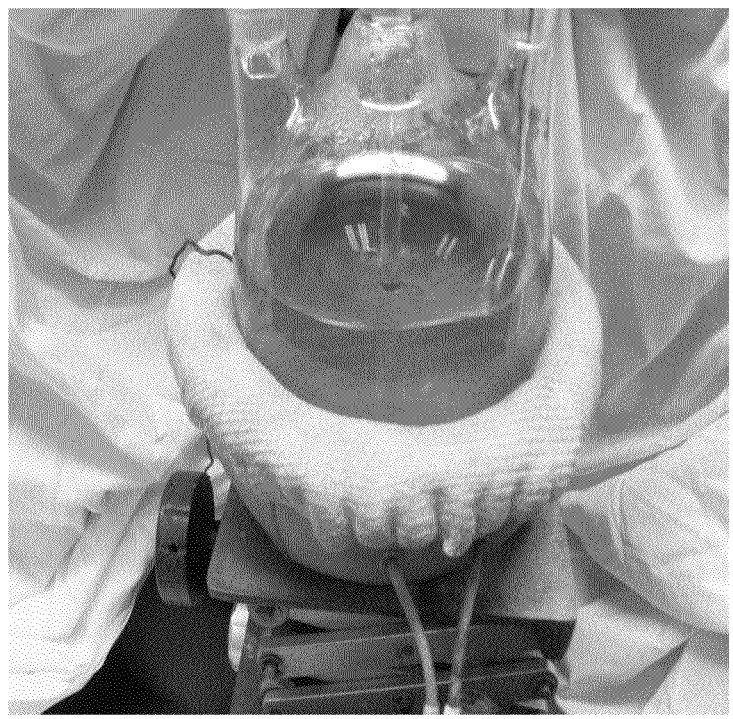

FIG. 10 is a photograph of the reaction mixture of Example 26 after 6 hours at 190° C. to 195° C. The reaction mixture is clear and pale yellow.

Figure 11:
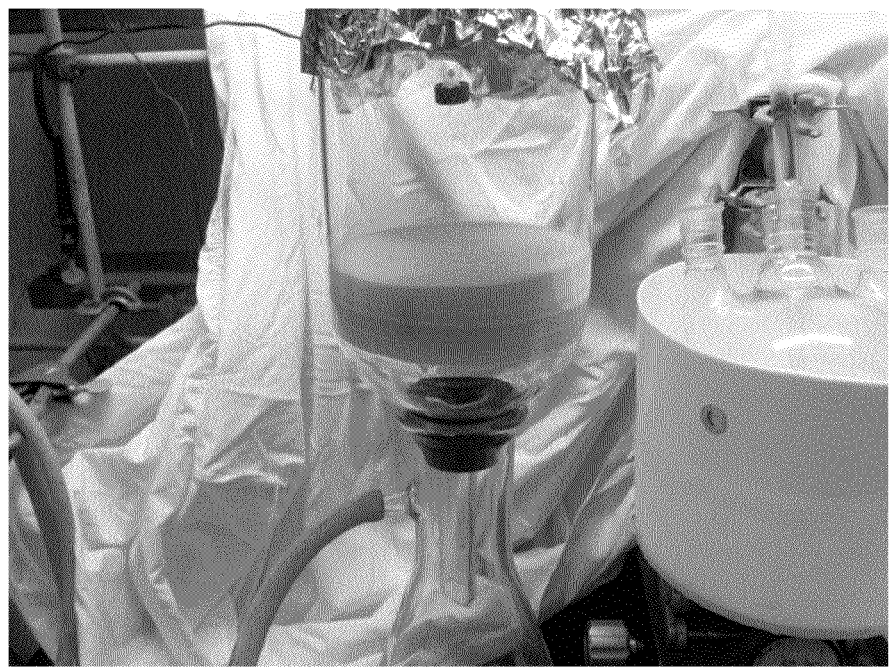

FIG. 11 is a photograph of BHET isolated from the depolymerization reaction of Example 26. Cooling the reaction mixture shown FIG. 10 resulted in crystallization of the BHET, which was isolated by direct filtration.

Figure 12:
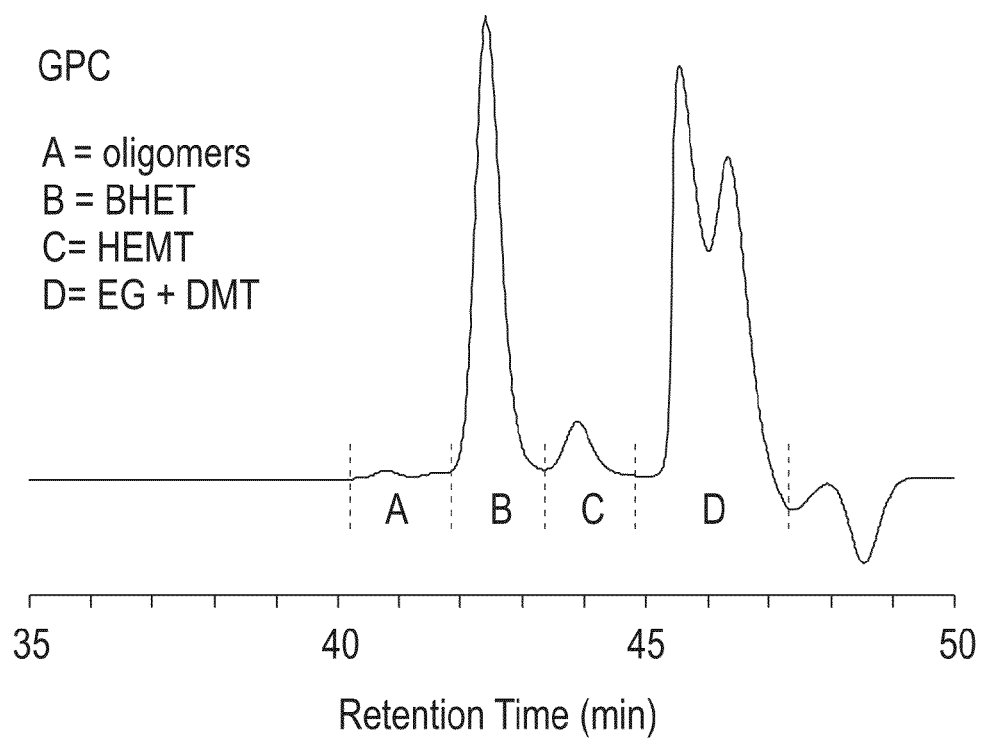

FIG. 12 is a graph of a typical GPC chromatogram of the crude product obtained by glycolysis of dimethyl terephthalate (DMT) with ethylene glycol at ambient temperature. Peak A is terephthalate oligomers, peak B is BHET, peak C is hydroxyethyl methyl terephthalate (HEMT), and peak(s) D is ethylene glycol and DMT.

DETAILED DESCRIPTION

Disclosed are methods of preparing monomeric dihydroxy terephthalate diesters by organocatalyzed depolymerization of terephthalate polyesters. Exemplary terephthalate polyesters include poly(ethylene terephthalate) (PET), poly(butylene terephthalate) (PBT), and copolymers thereof. The methods employ an amidine organocatalyst and/or an amidine salt organocatalyst and a glycol comprising 2 to 5 carbons. Unexpectedly, some glycols were found to be active co-catalysts with amidines, in addition to their roles as reactant and solvent in the depolymerizations. The dihydroxy terephthalate diesters can be produced in high yield and purity using a lower reaction temperature, shorter reaction time, lower molar amount of catalyst, and/or a lower molar amount of glycol compared to an otherwise identical depolymerization conducted by substituting the amidine organocatalyst with a cyclic guanidine (e.g., TBD) catalyst. Products of the depolymerization, which include terephthalate oligomers, such as dimer (contains two terephthalate aromatic rings) and trimer (contains three terephthalate aromatic rings), can be resubmitted for further reaction in a continuous depolymerization process.

The combination of the amidine and the glycol also produces a terephthalate reaction product containing less terephthalate oligomers compared to an otherwise identical depolymerization performed by substituting the amidine organocatalyst with an equimolar amount of guanidine organocatalyst. The term "terephthalate reaction product" refers to a product mixture whose components contain a terephthalate moiety, including terephthalate polyester, terephthalate oligomers, dihydroxy terephthalate diester, and the like. The term "terephthalate reaction product" excludes excess glycol, amidine organocatalyst, and other materials used in the reaction mixture that do not contain a terephthalate moiety.

Depolymerizations using a combination of the amidine and glycol were also observed to have shorter reaction times compared to an otherwise identical depolymerization conducted by substituting the glycol with a mono-alcohol.

No restriction is placed on the source of the terephthalate polyester. The terephthalate polyester can be a post-consumer product (e.g., beverage containers) and/or a terephthalate polyester that has not been used in the manufacture of a consumer product (e.g., newly formed terephthalate polyester, or a rejected product from a terephthalate polyester manufacturing plant). In an embodiment, the terephthalate polyester is a post-consumer poly(ethylene terephthalate) (PET) or a post-consumer poly(butylene terephthalate) (PBT).

The dihydroxy terephthalate diesters products of the depolymerization reaction have the general formula (1):

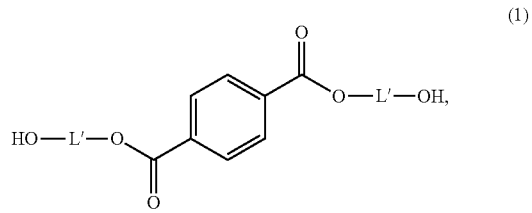

(1)

wherein each L' is an independent divalent group comprising 2 to 5 carbons. Exemplary L' groups include:

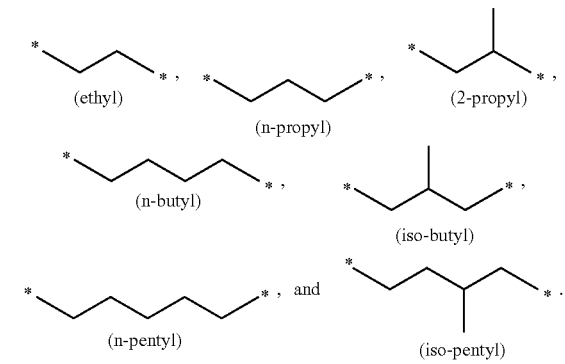

Herein, starred bonds represent attachment points.

A method comprises i) forming a reaction mixture comprising a terephthalate polyester, a glycol comprising 2 to 5 carbons, and an amidine organocatalyst, and ii) heating the reaction mixture at a temperature of about 120° C. or more to depolymerize the terephthalate polyester, thereby forming a terephthalate reaction product comprising a monomeric dihydroxy terephthalate diester. The terephthalate reaction product contains terephthalate oligomers in an amount less than the amount of terephthalate oligomers that would result from i) substituting the amidine organocatalyst with an equimolar amount of guanidine catalyst and ii) depolymerizing the terephthalate polyester under otherwise identical reaction conditions. The glycol can be used in an amount of about 4 to about 20 molar equivalents, or more preferably about 8 to about 16 molar equivalents, relative to total moles of terephthalate repeat unit of the polyester. The terephthalate reaction product can comprise 90 wt. % or more of a monomeric dihydroxy terephthalate diester based on a total weight of terephthalate reaction product, excluding solvent, amidine catalyst and other non-terephthalate components of the reaction mixture. The glycol can be a co-catalyst. Preferably, the reaction product comprises 0 wt. % to less than 10 wt. % of terephthalate oligomers.

The depolymerization reaction is preferably conducted under anhydrous conditions and a pressure of 1 atmosphere or more.

The terephthalate polyester can be depolymerized at a temperature in the range of about 120° C. to about 250° C., even more specifically about 120° C. to about 210° C., and still more specifically of about 120° C. to about 190° C., to produce a high yield of dihydroxy terephthalate diester. The depolymerization reaction can also be conducted at a lower temperature such as, for example, about 120° C. to about 180° C., about 130° C. to 180° C., about 120° C. to about 170° C., or about 130° C. to about 160° C. in less time compared to a depolymerization conducted under otherwise identical conditions using a cyclic guanidine, for example triazabicyclo[4.4.0]dec-5-ene (TBD). In an embodiment, the terephthalate polyester is a post-consumer PET or a post-consumer PBT.

In a preferred embodiment, the terephthalate polyester is poly(ethylene terephthalate) (PET), the glycol is ethylene glycol (EG), and the dihydroxy terephthalate diester is bis-(2-hydroxyethyl)terephthalate (BHET):

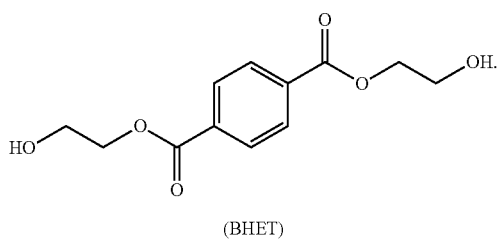 [SMILES: O=C(OCCO)c1ccc(C(=O)OCCO)cc1]

(BHET)

In another embodiment, the terephthalate polyester is poly(butylene terephthalate) (PBT), the glycol is 1,4-butanediol (BD), and the dihydroxy terephthalate diester is bis-(4-hydroxybutyl)terephthalate (BHBT):

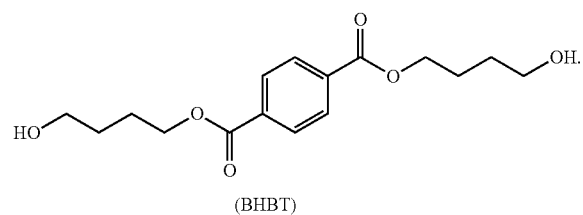

(BHBT)

The amidine organocatalyst has the general formula (2):

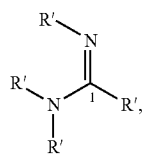

(2)

wherein each R' group is independently a monovalent radical comprising one or more carbons. The two nitrogens and central methine carbon labeled 1 in formula (2) are directly bonded only to a carbon of a substituent R' group. The central imine group,

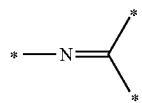

of formula (2) is not conjugated with another double bond. In an embodiment, the amidine organocatalyst is a compound containing only the elements carbon, nitrogen, and hydrogen.

By contrast, guanidines have a structure in which the methine carbon labeled 1 in formula (2) is bonded to a third nitrogen, as shown in formula (3):

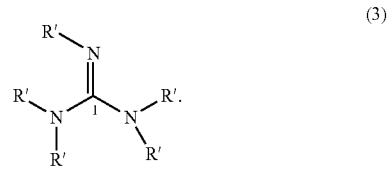

(3)

As will be shown in the examples, amidines are superior catalysts to guanidines in the depolymerization of terephthalate polyesters using glycols having 2 to 5 carbons.

The amidine functional group,

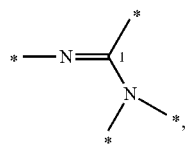

can reside in an acyclic structure or a cyclic structure. When the central methine carbon labeled 1 of the amidine functional group resides outside a ring, the amidine compound is referred to herein as an acyclic amidine. Non-limiting examples of acyclic amidines include N-methyl-N',N'-diethyl benzamidine and N-benzyl-N-phenyl-N'-p-tolyl-benzamidine. When the central methine carbon of the amidine functional group resides in a ring, the amidine compound is referred to as a cyclic amidine. No limitation is placed on the size of the ring that partially or wholly contains the cyclic amidine functional group. The cyclic amidine can comprise fused rings, non-fused rings, or a combination thereof. Non-limiting examples of cyclic amidine compounds include 1,8-diazabicyclo(5.4.0)undec-7-ene (DBU) and 1,5-diazabicyclo(4.3.0)non-5-ene (DBN).

The amidine organocatalyst can be polymer supported, meaning the amidine functional group is covalently linked to a polymer. The polymer supported amidine catalyst comprises one or more repeat units comprising a side chain comprising an acyclic amidine moiety and/or a cyclic amidine moiety. Polymer supported amidine catalysts include, for example, polystyrene bound 1,8-diazabicyclo(5.4.0)undec-7-ene) (DBU), referred to as PS-DBU available from Sigma-Aldrich.

In an embodiment, the amidine organocatalyst comprises one amidine functional group. In another embodiment, the amidine catalyst is a cyclic amidine catalyst selected from the group consisting of 1,8-diazabicyclo[5.4.0]undec-7-ene (DBU) [pKa (acetonitrile)=24.3, (water)=11.9], 1,5-diazabicyclo[4.3.0]non-5-ene (DBN) [pKa (water)=11.0], organic acid salts of the foregoing cyclic amidine catalysts, and combinations thereof.

Unexpectedly, amidine organocatalysts DBU and DBN were found to be more active catalysts for the depolymerization of post-consumer PET compared to triazabicyclo[4.4.0]dec-5-ene (TBD) [pKa (acetonitrile)=26.0]. DBU and DBN were found to be particularly active and selective catalysts in the glycolysis of PET with ethylene glycol. Computational studies supported this unique experimental result. TBD is usually thought of as a bi-functional catalyst that can potentially activate both an ester and ethylene glycol through hydrogen bonding. However, energy computations on transition state complexes formed during the transesterification of dimethyl terephthalate (DMT) by EG indicate that EG activates the terephthalate carbonyl more than TBD activates the terephthalate carbonyl. For this reason, the glycol EG is also a co-catalyst. Calculations also indicate that EG can activate the terephthalate carbonyl more than other glycol reagents can activate the terephthalate carbonyl. Reaction profile calculations further indicate that the mono-functional DBU catalyst activates EG more efficiently than the bi-functional TBD can activate EG. The calculations support the results observed in examples described further below, which show that amidine organocatalyzed depolymerization of PET by EG can be performed at a lower process temperature and lower process time while producing less oligomeric by-product compared to an otherwise identical TBD catalyzed depolymerization of PET by EG.

On the other hand, mono-alcohols do not activate the terephthalate carbonyl more than TBD activates the terephthalate carbonyl. When the depolymerization is performed using a mono-alcohol (e.g., octanol, benzyl alcohol) under otherwise identical conditions, the TBD catalyzed depolymerization is faster than the amidine catalyzed depolymerization.

The amidine organocatalyst can be in a salt form, such as an amidine salt of an organic acid. In some instances, the amidine salt organocatalysts have greater air stability and greater thermal stability at the depolymerization temperature (about 120° C. to about 250° C.) compared to the free base amidine organocatalyst. Also, the process time of the depolymerization reaction performed using the amidine salt organocatalyst can be about the same as the process time using the free base amidine organocatalyst. Additionally, the conjugate base of the acid component of the amidine salt catalyst can itself be an active catalytic species in the depolymerization reaction.

The amidine salt organocatalyst can be a pre-formed salt introduced as a separate component to the depolymerization reaction mixture. A method of preparing an amidine salt organocatalyst comprises i) treating an amidine base with an organic acid in a molar ratio of active hydroxy groups of the organic acid to amidine functional groups of 0.1:1.0 to 10.0:1.0, 0.5:1.0 to 2.0:1.0, or more particularly 0.8:1.0 to 1.2:1.0, thereby forming an amidine salt catalyst and ii) isolating the amidine salt catalyst. That is, the organic acid is present in the amidine salt organocatalyst in an amount of 0.1 to 10 molar equivalents relative to moles of the amidine base. Exemplary organic acids include acidic alcohols (e.g., phenols, fluorinated phenols, and other fluorinated alcohols), carboxylic acids, sulfonic acids, sulfinic acids, organophosphates, organophosphonates, organophosphinic acids, sulfuric acid, phosphoric acid, phosphorous acid, and phosphinic acid. The organic acids can be used singularly or in combination.

In an embodiment, the amidine salt organocatalyst comprises an aromatic carboxylic acid salt of DBU and/or DBN. Non-limiting aromatic carboxylic acids include, for example, benzoic acid, terephthalic acid, and monoesters of terephthalic acid. In another embodiment, the amidine salt organocatalyst comprises an aromatic sulfonic acid salt of DBU and/or DBN. Aromatic sulfonic acids include, for example, benzene sulfonic acid and p-toluene sulfonic acid (pTSA).

Alternatively, the amidine salt organocatalyst can be prepared in situ. A method of depolymerizing a terephthalate polyester comprises i) forming a reaction mixture comprising a glycol comprising 2 to 5 carbons, a terephthalate polyester, an amidine organocatalyst, and an organic acid, and ii) heating the reaction mixture at a temperature of about 120° C. or more to depolymerize the terephthalate polyester, thereby forming a terephthalate reaction product comprising a monomeric dihydroxy terephthalate diester. The order of addition of the organic acid, glycol, terephthalate polyester, and amidine organocatalyst can be in any suitable order. In an embodiment, the terephthalate reaction product contains terephthalate oligomers in an amount less than the amount of terephthalate oligomers that would be produced by i) substituting the amidine organocatalyst with an equimolar amount of guanidine catalyst and ii) depolymerizing the terephthalate polyester under otherwise identical reaction conditions. The glycol can be a co-catalyst. The glycol can be used in an amount of about 4 to about 20 molar equivalents, more particularly about 8 to about 16 molar equivalents, and even more specifically 8 to 12 molar equivalents compared to total moles of terephthalate repeat unit of the polyester. The terephthalate reaction product can comprise 90 wt. % or more of a monomeric dihydroxy terephthalate diester based on a total weight of terephthalate reaction product, excluding solvent, amidine catalyst and other non-terephthalate components of the reaction mixture. Preferably, the reaction product comprises 0 wt. % to less than 10 wt. % of terephthalate oligomers. In an embodiment, the glycol is used in an amount of about 8 to about 12 molar equivalents relative to total moles of terephthalate repeat unit in the terephthalate polyester.

In an embodiment, the glycol and the amidine organocatalyst or the pre-formed amidine salt organocatalyst are combined at ambient temperature (18° C. to 28° C.), thereby forming a premix, and the premix is added to the terephthalate polyester at ambient temperature.

The terephthalate polyester can be depolymerized using a pre-formed or an in situ generated amidine salt organocatalyst at a temperature of about 120° C. or more, more specifically at a temperature in the range of about 120° C. to about 250° C., about 120° C. to about 210° C., or about 120° C. to about 190° C. Even more specifically, the reaction can be conducted at a temperature less than 190° C., such as, for example, a temperature in the range about 120° C. to about 180° C., about 130° C. to 180° C., about 120° C. to about 170° C., or about 130° C. to about 160° C.

The organic acid can be a polymeric organic acid, for example poly(acrylic acid), poly(methacrylic acid), poly(styrene sulfonic acid), copolymers of the foregoing, and combinations thereof. The polymeric organic acid can be a linear polymer, a branched polymer, a block copolymer, or a combination thereof. The polymeric organic acid can be highly crosslinked in the form of a bead. The amidine salt organocatalyst can be a pre-formed salt comprising a polymeric organic acid and an amidine organocatalyst, or an in situ generated salt of a polymeric organic acid and an amidine organocatalyst.

In an embodiment, the organic acid is selected from the group consisting of benzoic acid (BA), terephthalic acid, p-toluenesulfonic acid (pTSA), tetrakis(trifluoromethyl)-1,3-benzene dimethanol (PFA), and phenol.

The amidine salt organocatalyst can be a pre-formed salt of a polymer supported amidine organocatalyst and an organic acid, or an in situ generated salt thereof.

The chemical formulas of the amidine organocatalyst, the pre-formed amidine salt organocatalyst, and the in situ generated amidine salt organocatalyst, which includes the chemical formulas of the amidine organocatalyst and the organic acid, preferably do not contain any of the following restricted metals: ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

No restriction is placed on the presence of boron, silicon, or any individual alkali metal in the chemical formulas of the amidine organocatalyst and the amidine salt organocatalyst, as long as the depolymerization reaction produces a dihydroxy terephthalate diester in a desirable yield and purity.

The amidine organocatalyst and/or the amidine salt organocatalyst can be present in the depolymerization reaction mixture in an amount greater than 0 molar equivalents to less than about 0.3 molar equivalents (30 mol %), more particularly 0.001 to 0.1 molar equivalents (0.1 to 10 mol %), 0.001 to 0.05 molar equivalents (0.1 to 5 mol %), 0.001 to 0.01 molar equivalents (0.1 to 1.0 mol %), or 0.001 to 0.005 molar equivalents (0.1 to 0.5 mol %) relative to total moles of terephthalate repeat unit present in the terephthalate polyester.

The poly(ethylene terephthalate) repeat unit (i.e., PET repeat unit) has the structure:

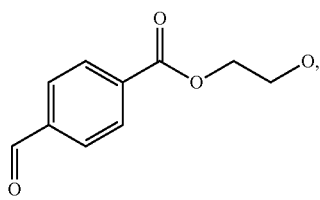

which has a molecular weight of 192.

The poly(butylene terephthalate) repeat unit (i.e., PBT repeat unit) has the structure:

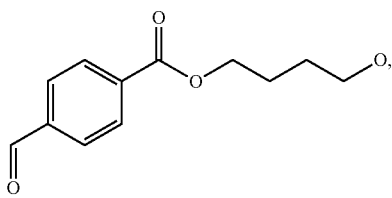

which has a molecular weight of 220.

The terephthalate polyester is not limited to a linear homopolymer. For example, terephthalate polyester can include branched, hyperbranched, dendritic, cyclic, and/or star-shaped architectures. The terephthalate polyester can comprise a copolymer, for example random copolymer, block copolymer, multiblock copolymer, alternating copolymer, terpolymers, and the like. In an embodiment, the terephthalate polyester is a poly(ethylene terephthalate-co-butylene terephthalate) copolymer comprising PBT repeat units and PET repeat units.

The terephthalate polyester can be obtained from any suitable source, which can include used consumable goods such as beverage bottles, food containers, other liquid containers, packaging, and/or synthetic fibers. In preparation for the depolymerization of the terephthalate polyester, the used consumable goods can be treated by one or more processes, including but not limited to: i) sorting, ii) pre-washing, iii) coarse cutting, iv) removal of stones, glass and metal, v) air sifting to remove film, paper and labels, vi) grinding, dry and/or wet, vii) removal of poly(vinyl chloride), high density poly(ethylene), low density poly(ethylene), and/or other polymers, viii) hot wash, ix) caustic wash, x) caustic surface etching, xi) rinsing, xii) clean water rinsing, xiii) drying, xiv) air sifting of flakes, and xv) flake sorting. The foregoing processes can be used singularly or in combination, in any desirable order to prepare terephthalate polyester for the depolymerization reaction.

The terephthalate polyester can be in the form of a chip, flake, granule, powder, and/or other particle form that preferably does not become airborne dust in a manufacturing plant.

The terephthalate polyester can contain other polymers, including poly(vinyl chloride) in an amount of 0 wt. % to 5 wt. %, 0 wt. % to 1 wt. %, 0 wt. % to 0.1 wt. %, and more specifically in an amount of 0 wt. % to 0.001 wt. % based on a total weight of the post-consumer terephthalate polyester. The terephthalate polyester can contain low density polyethylene (LDPE) and/or high density polyethylene (HDPE) in an amount of 0 wt. % to 5 wt. %, 0 wt. % to 1 wt. %, 0 wt. % to 0.1 wt. %, and more specifically in an amount of 0 wt. % to 0.001 wt. % based on a total weight of the terephthalate polyester.

The depolymerization reaction mixture comprises a glycol comprising 2 to 5 carbons. The glycol can be branched or non-branched. In a preferred embodiment, the glycol is a linear glycol selected from the group consisting of 1,2-ethanediol (ethylene glycol), 1,3-propanediol, and 1,4-butanediol, and 1,5-pentanediol. In an embodiment, the glycol is ethylene glycol (EG) and/or 1,4-butanediol (BD).

The glycol can be present in the reaction mixture in an amount of about 1 to about 20 molar equivalents relative to total moles of terephthalate repeat unit present in the terephthalate polyester, more particularly about 4 to about 20 molar equivalents, about 4 to about 16 molar equivalents, about 6 to about 16 molar equivalents, or about 8 to about 16 molar equivalents. Even more particularly the glycol can be used in an amount less than 16 molar equivalents such as, for example, about 4 to about 12 molar equivalents, about 6 to about 12 molar equivalents, or about 8 to 12 molar equivalents relative to total moles of terephthalate repeat unit present in the terephthalate polyester. In a specific embodiment, the glycol is present in an amount of about 8 to about 12 molar equivalents relative to total moles of terephthalate repeat unit present in the terephthalate polyester, and the terephthalate reaction product contains terephthalate oligomers in an amount less than about 10 wt. % based on a total weight of the terephthalate reaction product.

The depolymerization of the terephthalate polyester can be carried out in an inert atmosphere or in the air. The depolymerization can be conducted under pressure ranging from 0.01 to 1000 atmospheres (atm), preferably 0.1 to 100 atm, more preferably 1 atm. The depolymerization requires no additional solvent; that is, the glycol is the solvent.

The reaction mixture is typically, although not necessarily, agitated (e.g., stirred). The progress of the reaction can be monitored by standard techniques (e.g., NMR, GPC, and HPLC), although visual inspection is generally sufficient, insofar as a transparent reaction mixture indicates that the polymer has reacted to an extent sufficient to allow all solid material to dissolve.

The dihydroxy terephthalate diester can be present in the crude product in an amount of 50 wt. % to 100 wt. %, 90 wt. % to 100 wt. %, 94 wt. % to 100 wt. %, or more particularly 96 wt. % to 100 wt. %, based on the weight of the terephthalate reaction product. The terephthalate oligomers can be present in the crude product in an amount of 0 wt. % to less than 10 wt. %, more particularly 0 wt. % to 6 wt. %, and even more particularly 0 wt. % to 4 wt. % based on the weight of terephthalate reaction product.

The dihydroxy terephthalate diester can be isolated by methods that include recrystallization, extraction, direct filtration, distillation, or combinations thereof. For large scale production, direct filtration and distillation are more preferred methods of isolation of the product dihydroxy terephthalate diester. Ion exchange resins can be employed to remove metals in the terephthalate polyester. In direct filtration, the reaction mixture containing the depolymerized terephthalate polyester is cooled to ambient temperature, the dihydroxy terephthalate ester is allowed to precipitate as a crystalline solid, and the solid is isolated by filtration.

The above described methods are particularly suitable for preparing bis(2-hydroxyethyl)terephthalate (BHET) by depolymerization of poly(ethylene terephthalate). A particular method comprises forming a reaction mixture comprising poly(ethylene terephthalate) (PET), ethylene glycol in an amount of 4 to about 20 molar equivalents relative to a poly(ethylene terephthalate) repeat unit, and an amidine organocatalyst; and heating the reaction mixture at a temperature in the range of about 120° C. to about 210° C. to depolymerize the poly(ethylene terephthalate), thereby producing a terephthalate reaction product comprising the bis(2-hydroxyethyl) terephthalate (BHET). An organic acid can be included in the reaction mixture before depolymerizing the poly(ethylene terephthalate). The organic acid can be an aromatic carboxylic acid, preferably terephthalic acid and/or benzoic acid. Alternatively, the amidine organocatalyst can be substituted with a pre-formed amidine salt organocatalyst, which is added to the reaction mixture. The terephthalate reaction product can comprise 90 wt. % or more of the bis(2-hydroxyethyl) terephthalate (BHET) based on total weight of the terephthalate reaction product.

When an amidine organocatalyst is used, the terephthalate reaction product contains terephthalate oligomers in an amount less than the amount of terephthalate oligomers that would result from i) substituting the amidine organocatalyst with an equimolar amount of a guanidine catalyst and ii) depolymerizing the poly(ethylene terephthalate) under otherwise identical reaction conditions. When an amidine salt organocatalyst is used, the depolymerization produces a terephthalate reaction product that contains terephthalate oligomers in an amount less than the amount of terephthalate oligomers that would result from i) substituting the amidine salt organocatalyst with an equimolar amount of a guanidine salt catalyst prepared using a guanidine base and the organic acid, and ii) depolymerizing the poly(ethylene terephthalate) under otherwise identical reaction conditions.

In an embodiment, the amidine organocatalyst is selected from the group consisting of DBU, DBN, polymer supported DBU, polymer supported DBN, and combinations thereof. In another embodiment, ethylene glycol is present in an amount of about 8 to about 12 molar equivalents relative to moles of the PET repeat unit, the amidine organocatalyst is DBU, and the terephthalate reaction product contains less than 10 wt. % of terephthalate oligomers based on total weight of the terephthalate reaction product. In another embodiment, the depolymerization is conducted at a temperature in the range of about 120° C. to about 190° C. In another embodiment, the depolymerization is conducted at a temperature in the range of about 120° C. to about 180° C. In another embodiment, the poly(ethylene terephthalate) is post-consumer poly(ethylene terephthalate). In another embodiment, the pre-formed amidine salt organocatalyst is a carboxylic acid salt of an amidine base selected from the group consisting of DBU, DBN, polymer supported DBU, polymer supported DBN, and combinations thereof. In another embodiment, the BHET is isolated by direct filtration.

The above described methods are also particularly suitable for preparing bis(4-hydroxybutyl)terephthalate (BHBT). A particular method comprises forming a reaction mixture comprising poly(butylene terephthalate) (PBT), an amidine organocatalyst, and 4 to 20 molar equivalents of 1,4-butanediol relative to moles of poly(butylene terephthalate) repeat unit present in the PBT; and heating the reaction mixture at a temperature in the range of about 120° C. to about 210° C. to depolymerize the poly(butylene terephthalate), thereby forming a terephthalate reaction product comprising bis(4-hydroxybutyl)terephthalate (BHBT). An organic acid can be included in the reaction mixture before depolymerizing the poly(butylene terephthalate). The organic acid can be an aromatic carboxylic acid, preferably terephthalic acid and/or benzoic acid. Alternatively, the amidine organocatalyst can be substituted with a pre-formed amidine salt organocatalyst, which is added to the reaction mixture. The terephthalate reaction product can comprise 90 wt. % or more of the bis(4-hydroxybutyl)terephthalate (BHBT) based on total weight of the terephthalate reaction product.

When an amidine organocatalyst is used, the terephthalate reaction product contains terephthalate oligomers in an amount less than the amount of terephthalate oligomers that would result from i) substituting the amidine organocatalyst with an equimolar amount of a guanidine catalyst and ii) depolymerizing the poly(butylene terephthalate) under otherwise identical reaction conditions. When an amidine salt organocatalyst is used, the depolymerization produces a terephthalate reaction product that contains terephthalate oligomers in an amount less than the amount of terephthalate oligomers that would result from i) substituting the amidine salt organocatalyst with an equimolar amount of a guanidine salt catalyst prepared using a guanidine base and the organic acid, and ii) depolymerizing the poly(butylene terephthalate) under otherwise identical reaction conditions.

In an embodiment, the amidine organocatalyst is selected from the group consisting of DBU, DBN, polymer supported DBU, polymer supported DBN, and combinations thereof. In another embodiment, 1,4-butanediol is present in an amount of about 8 to about 12 molar equivalents relative to moles of the PBT repeat unit, the amidine organocatalyst is DBU, and the terephthalate reaction product contains less than 10 wt. % of terephthalate oligomers based on total weight of the terephthalate reaction product. In another embodiment, the depolymerization is conducted at a temperature in the range of 120° C. to 190° C. In another embodiment, the depolymerization is conducted at a temperature in the range of 120° C. to 180° C. In another embodiment, the poly(butylene terephthalate) is a post-consumer poly(butylene terephthalate). In another embodiment, the pre-formed amidine salt organocatalyst is a carboxylic acid salt of an amidine base selected from the group consisting of DBU, DBN, polymer supported DBU, polymer supported DBN, and combinations thereof.

The examples that follow illustrate the practice of the disclosed methods.

EXAMPLES

Materials purchased or prepared in the following examples are listed in Table 1.

TABLE 1

| ABBREVIATION | DESCRIPTION | SUPPLIER |
|---|---|---|
| PET | Post-consumer Poly(Ethylene Terephthalate), Flakes | Arrowhead |
| PBT | Poly(Butylene Terephthalate) | Sigma-Aldrich |
| DBU | 1,8-Diazabicycloundec-7-ene | Sigma-Aldrich |
| DBN | 1,5-Diazabicyclo[4.3.0]non-5-ene | Sigma-Aldrich |
| TBD | Triazabicyclo[4.4.0]dec-5-ene | Sigma-Aldrich |
| PFA | Tetrakis(trifluoromethyl)-1,3-Benzene Dimethanol | Sigma-Aldrich |
| PS-DBU | Polystyrene bound-1,8-Diazabicycloundec-7-ene | Sigma-Aldrich |
| BHET | Bis-(Hydroxyethyl) Terephthalate (MW 254) | (preparation described below) |
| BHBT | Bis-(hydroxybutyl) Terephthalate (MW 310) | (preparation described below) |
| BHPT | Bis-(hydroxypropyl) terephthalate (MW 282) | (preparation described below) |
| BHHT | Bis-(hydroxyhexyl) terephthalate (MW 366) | (preparation described below) |
| EG | Ethylene glycol | Sigma-Aldrich |
| PD | 1,3-Propanediol | Sigma-Aldrich |
| BD | 1,4-Butanediol | Spectrum Chemicals |
| HD | 1,6-Hexanediol | Sigma-Aldrich |
| BzOH | Benzyl Alcohol | Sigma-Aldrich |
| OD | 1-Octanol | Sigma-Aldrich |
| pTSA | p-Toluenesulfonic Acid | Sigma-Aldrich |
| BA | Benzoic Acid | Sigma-Aldrich |
| DMAP | 4-(N,N-Dimethylamino)pyridine | Sigma-Aldrich |
| DABCO | 1,4-Diazabicyclo[2.2.2]octane | Sigma-Aldrich |
| NMI | N-Methylimidazole | Sigma-Aldrich |
| DMA | N,N-Dimethylaniline | Sigma-Aldrich |
| DMT | Dimethyl Terephthalate | Sigma-Aldrich |

Purchased materials were used as received.

Post-Consumer PET.

The post-consumer PET was obtained as bottles (Arrowhead). The bottles were washed with water, dried in air at ambient temperature, and shredded by hand to a size of about 3 square millimeters to 5 square millimeters. The flakes were dried again in vacuum at 80° C. for at least 12 hours prior to the depolymerization reaction. The metal content of the post-consumer PET was below the detection limit of the analytical equipment, which was about 0.01 to about 0.05 weight percent of the total weight of the post-consumer PET. The glass transition temperature of the post-consumer PET was 77° C., the melting point was 252° C., and the 5% weight loss temperature was 376° C.

Preparation of Amidine Salt Organocatalysts.

Preparation of salt organocatalyst SC-1 (DBU-BA, 1:1 m/m). A THF solution (5 mL) of benzoic acid (BA; 0.61 g, 5.0 mmol) was added to a 50 mL flask containing THF (10 mL) and DBU (0.76 g, 5.0 mmol) under nitrogen atmosphere. The solution was stirred for 3 hours and evaporated afterward. The powdery residue was then washed with diethyl ether, filtered, and dried under vacuum (1.25 g, 91%).

Preparation of salt organocatalyst SC-2 (DBU-Phenol, 1:1 m/m). A THF solution (5 mL) of phenol (0.48 g, 5.1 mmol) was added to a 50 mL flask containing THF (10 mL) and DBU (0.76 g, 5.0 mmol) under nitrogen atmosphere. The solution was stirred for 2 hours and evaporated afterward. The liquid residue was then washed with diethyl ether, isolated by decantation, and dried under vacuum (1.18 g, 95%).

Glycolysis of PET by Ethylene Glycol (EG).

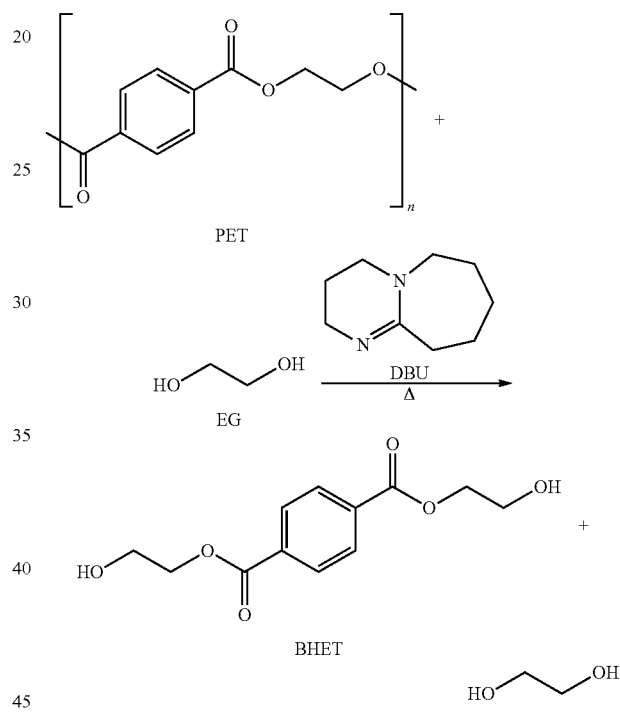

Example 1

Figure 1:
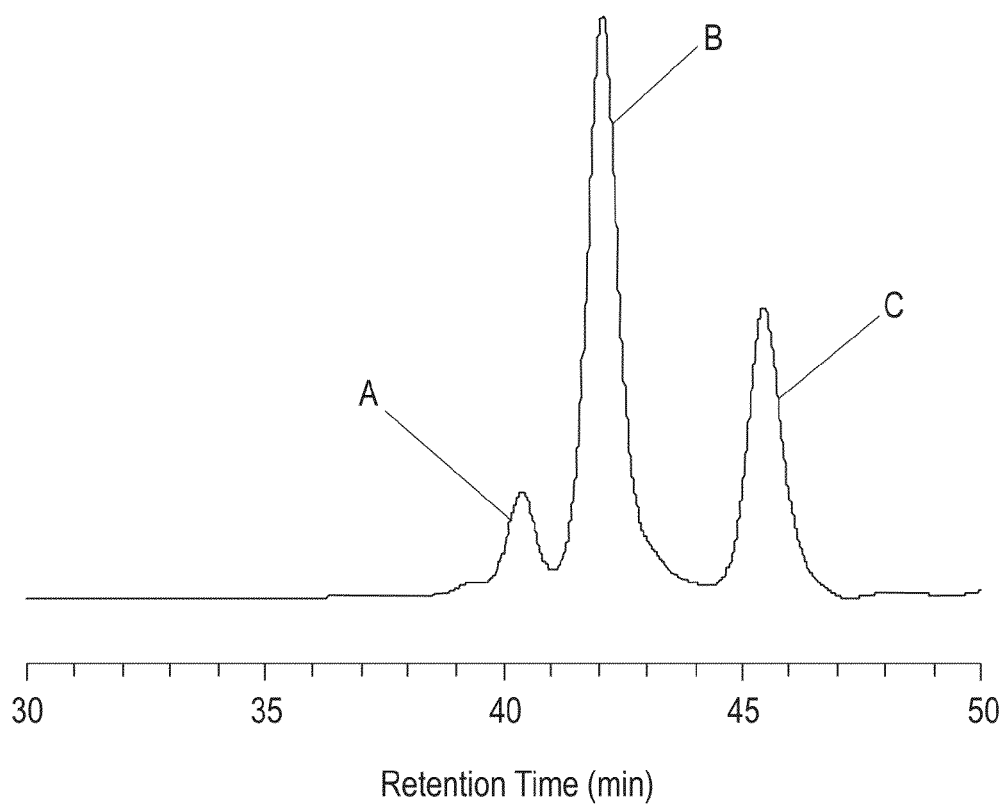
FIG. 1 is a typical gel permeation chromatography (GPC) chart of the crude glycolysis product formed in the glycolysis reaction of poly(ethylene terephthalate) (PET) in excess ethylene glycol (EG).

Use of 10 mol % DBU. To a 25 ml Schlenk tube containing post-consumer PET flakes (0.96 g, 5.0 mmol) was charged a mixture of ethylene glycol (EG) (4.96 g, 80 mmol) and 1,8-diazabicycloundec-7-ene (DBU) (76 mg, 0.50 mmol). The tube was immersed in an oil bath and heated with stirring at 190° C. The slurry turned into a clear and homogeneous liquid in 6.5 minutes. Aliquots of the crude product were taken for $^1$H NMR and GPC analysis in order to evaluate the contents. The crude depolymerization products obtained in the above reaction consist of bis(2-hydroxyethyl)terephthalate (BHET), PET oligomers comprising mainly dimer and trimer, and excess EG. FIG. 1 is a typical gel permeation chromatogram (GPC) of the crude glycolysis products formed by the depolymerization reaction. Peak A corresponds to PET oligomers, peak B corresponds to BHET, and peak C corresponds to EG. GPC peak A corresponds to PET oligomers, GPC peak B corresponds to BHET, and peak GBC peak C is EG. Based on a ratio of the area of GPC peak A (PET oligomers) to the area of GPC peak B (BHET), the BHET can be formed in yields of 90% or more. In Example 1, BHET: PET oligomers=98.9:1.1 w/w based on the ratio of the area of the B peak (BHET) to the area of the A peak (PET oligomer) normalized to 100%.

Example 2

Use of 5 mol % DBU. To a 25 ml Schlenk tube containing PET flakes (0.48 g, 2.5 mmol) was charged a mixture of EG (2.48 g, 40 mmol) and DBU (38 mg, 0.25 mmol). The tube was immersed in an oil bath and heated with stirring at 190° C. The slurry turned into a clear and homogeneous liquid in 5 minutes. Aliquots of the crude product were taken for $^1$H NMR and GPC analysis in order to evaluate the content. BHET:PET oligomer=98.8:1.2 w/w.

The crude BHET product was purified in several ways, as follows:

a) Recrystallization. The crude product was poured in deionized water (100 ml) while being warm. The insoluble fraction was isolated by filtration and the filtrate was then left in a refrigerator (4° C.) for 24 hours. The crystals formed were filtered and dried in vacuum to yield the product (0.52 g, 81%).

b) Extraction. The crude product was cooled down to ambient temperature and dissolved in methylene chloride (100 ml) and washed with 0.5 N HCl aqueous solution (100 ml) that was then re-extracted with methylene chloride (50 ml). These two organic fractions were combined, stirred over MgSO4, evaporated, and dried in vacuum to give the product (0.42 g, 66%).

c) Direct filtration. The crude product was cooled down to ambient temperature to allow for crystallization of the product. The slurry was then filtered and the residual crystals were washed with a minimum amount of water (about 10 ml). Finally the crystals were dried under vacuum to give the product (0.40 g, 63%).

Example 3

Use of 10 mol % DBN. To a 25 ml Schlenk tube containing PET flakes (0.96 g, 5.0 mmol) was charged a mixture of EG (4.96 g, 80 mmol) and DBN (65 mg, 0.5 mmol). The tube was immersed in an oil bath and heated with stirring at 190° C. The slurry turned into a clear and homogeneous liquid in 7 minutes. Aliquots of the crude product were taken for $^1$H NMR and GPC analysis in order to evaluate the content. BHET:PET oligomer=98.5:1.5 w/w.

Example 4

Use of 10 mol % pre-formed salt organocatalyst SC-1 (DBU-BA, 1:1 m/m). To a 25 ml Schlenk tube containing PET flakes (0.48 g, 2.5 mmol) was charged a mixture of EG (2.48 g, 40 mmol) and pre-formed salt organocatalyst SC-1 (68 mg, 0.25 mmol). The tube was immersed in an oil bath and heated with stirring at 190° C. The slurry turned into a clear and homogeneous liquid in 40 minutes. Aliquots of the crude product were taken for $^1$H NMR and GPC analysis in order to evaluate the content. BHET:PET oligomer=92.8:7.2 w/w.

Example 5

Use of 10 mol % in situ generated salt organocatalyst DBU-BA (1:1 m/m) salt organocatalyst, 2.5 mmol PET. To a 25 ml Schlenk tube containing PET flakes (0.48 g, 2.5 mmol) was charged a mixture of EG (2.48 g, 40 mmol), DBU (38 mg, 0.25 mmol), and BA (30 mg, 0.25 mmol). The tube was immersed in an oil bath and heated with stirring at 190° C. The slurry turned into a clear and homogeneous liquid in 45 minutes. Aliquots of the crude product were taken for $^1$H NMR and GPC analysis in order to evaluate the content. BHET:PET oligomer=92.6:7.4 w/w.

Example 6

Use of 10 mol % in situ generated salt organocatalyst DBU-BA (1:1 m/m), 5.0 mmol PET. To a 25 ml Schlenk tube containing PET flakes (0.96 g, 5.0 mmol) was charged a mixture of EG (4.96 g, 80 mmol), DBU (77 mg, 0.5 mmol), and BA (61 mg, 0.5 mmol). The tube was immersed in an oil bath and heated with stirring at 190° C. The slurry turned into a clear and homogeneous liquid in 38 minutes. Aliquots of the crude product were taken for $^1$H NMR and GPC analysis in order to evaluate the content. BHET:PET oligomer=93.8:6.2 w/w.

Example 7

Use of 10 mol % pre-formed salt organocatalyst SC-2 (DBU-Phenol, 1:1 m/m). To a 25 ml Schlenk tube containing PET flakes (0.48 g, 2.5 mmol) was charged a mixture of EG (2.48 g, 40 mmol) and preformed salt organocatalyst SC-2 (66 mg, 0.27 mmol). The tube was immersed in an oil bath and heated with stirring at 190° C. The slurry turned into a clear and homogeneous liquid in 9 minutes. Aliquots of the crude product were taken for $^1$H NMR and GPC analysis in order to evaluate the content. BHET:PET oligomer=96.7:3.3 w/w.

Example 8

Use of 10 mol % of in situ generated salt organocatalyst DBU-Phenol (1:1 m/m). To a 25 ml Schlenk tube containing PET flakes (0.96 g, 5.0 mmol) was charged a mixture of EG (4.96 g, 40 mmol), DBU (76 mg, 0.5 mmol), and phenol (47 mg, 0.5 mmol). The tube was immersed in an oil bath and heated with stirring at 190° C. The slurry turned into a clear and homogeneous liquid in 8 minutes. Aliquots of the crude product were taken for $^1$H NMR and GPC analysis in order to evaluate the content. BHET:PET oligomer=92.6:7.4 w/w.

Example 9

Use of 10 mol % of in situ generated salt organocatalyst DBU-PFA (2:1 m/m) (PFA=tetrakis(trifluoromethyl)-1,3-benzene dimethanol), 2.5 mmol PET. To a 25 ml Schlenk tube containing PET flakes (0.48 g, 2.5 mmol) was charged a mixture of EG (2.48 g, 40 mmol), DBU (38 mg, 0.25 mmol), and PFA (51 mg, 0.125 mmol). The tube was immersed in an oil bath and heated with stirring at 190° C. The slurry turned into a clear and homogeneous liquid in 8 minutes. Aliquots of the crude product were taken for $^1$H NMR and GPC analysis in order to evaluate the content. BHET:PET oligomer=95.3:4.7 w/w.

Example 10

Use of 10 mol % of in situ generated salt organocatalyst DBU-PFA (2:1 m/m), 5 mmol PET. To a 25 ml Schlenk tube containing PET flakes (0.96 g, 5.0 mmol) was charged a mixture of EG (4.97 g, 80 mmol), DBU (76 mg, 0.5 mmol), and PFA (102 mg, 0.25 mmol). The tube was immersed in an oil bath and heated with stirring at 190° C. The slurry turned into a clear and homogeneous liquid in 8 minutes. Aliquots of the crude product were taken for $^1$H NMR and GPC analysis in order to evaluate the content. BHET:PET oligomer=95.8:4.2 w/w.

Example 11

Use of 10 mol % in situ generated salt organocatalyst DBU/p-TSA (1:1 m/m) (pTSA=p-toluenesulfonic acid). To a 25 ml Schlenk tube containing PET flakes (0.96 g, 5.0 mmol) was charged a mixture of EG (4.96 g, 80 mmol), DBU (77 mg, 0.5 mmol), and pTSA (96 mg, 0.50 mmol). The tube was immersed in an oil bath and heated with stirring at 190° C. The slurry turned into a clear and homogeneous liquid in 1120 minutes. Aliquots of the crude product were taken for $^1$H NMR and GPC analysis in order to evaluate the content. BHET:PET oligomer=91.9:8.1 w/w.

Example 12

Use of 10 mol % of polystyrene supported DBU organocatalyst PS-DBU. To a 25 ml Schlenk tube containing PET flakes (0.48 g, 2.5 mmol) was charged a mixture of EG (2.51 g, 40 mmol) and PS-DBU (435 mg, 0.25 mmol). The tube was immersed in an oil bath and heated with stirring at 190° C. The slurry turned into a clear and homogeneous liquid in 180 minutes. Aliquots of the crude product were taken for $^1$H NMR and GPC analysis in order to evaluate the content. BHET:PET oligomer=93.4:6.6 w/w.

Example 13

Use of 10 mol % in situ generated salt organocatalyst PS-DBU-BA (1:1 m/m) salt. To a 25 ml Schlenk tube containing PET flakes (0.48 g, 2.5 mmol) was charged a mixture of EG (2.48 g, 40 mmol), PS-DBU (437 mg, 0.25 mmol), and BA (31 mg, 0.25 mmol). The tube was immersed in an oil bath and heated with stirring at 190° C. The slurry turned into a clear and homogeneous liquid in 360 minutes. Aliquots of the crude product were taken for $^1$H NMR and GPC analysis in order to evaluate the content. BHET:PET oligomer=92.6:7.4 w/w.

Example 14

Use of 10 mol % DBU exposed to the air for 24 hours. DBU (39 mg, 0.25 mmol) was taken in a 5 mL glass vial and the vial was left on a bench for 24 hours without the lid. EG (2.49 g, 40 mmol) was added in the vial and the mixture was charged to a 25 ml Schlenk tube containing PET flakes (0.49 g, 2.5 mmol). The tube was immersed in an oil bath and heated with stirring at 190° C. The slurry turned into a clear and homogeneous liquid in 35 minutes. Aliquots of the crude product were taken for $^1$H NMR and GPC analysis in order to evaluate the content. BHET:PET oligomer=94.9:5.1 w/w.

Example 15

Use of 10 mol % pre-formed salt organocatalyst SC-1 (DBU-BA, 1:1 m/m) salt exposed to the air for 24 hours. SC-1 (70 mg, 0.26 mmol) was placed in a 5 mL glass vial and the vial was left on a bench for 24 hours without the lid. EG (2.49 g, 40 mmol) was added to the salt and the mixture was charged to a 25 ml Schlenk tube containing PET flakes (0.48 g, 2.5 mmol). The tube was immersed in an oil bath and heated with stirring at 190° C. The slurry turned into a clear and homogeneous liquid in 45 minutes. Aliquots of the crude product were taken for $^1$H NMR and GPC analysis in order to evaluate the content. BHET:PET oligomer=95.4:4.6 w/w.

Example 16

Use of 10 mol % pre-formed salt organocatalyst SC-2 (DBU-Phenol, 1:1 m/m) exposed to the air for 24 hours. SC-2 (64 mg, 0.26 mmol) was placed in a 5 mL glass vial and the vial was left on a bench for 24 hours without the lid. EG (2.49 g, 40 mmol) was added to the salt and the mixture was charged to a 25 ml Schlenk tube containing PET flakes (0.48 g, 2.5 mmol). The tube was immersed in an oil bath and heated with stirring at 190° C. The slurry turned into a clear and homogeneous liquid in 26 minutes. Aliquots of the crude product were taken for $^1$H NMR and GPC analysis in order to evaluate the content. BHET:PET oligomer=94.2:5.8 w/w.

Example 17

Use of 10 mol % in situ generated salt organocatalyst DBU-BA 1:2 m/m. To a 25 ml Schlenk tube containing PET flakes (0.48 g, 2.5 mmol) was charged a mixture of EG (2.50 g, 40 mmol), DBU (38 mg, 0.25 mmol), and BA (62 mg, 0.51 mmol). The tube was immersed in an oil bath and heated with stirring at 190° C. The slurry turned into a clear and homogeneous liquid in 150 minutes. Aliquots of the crude product were taken for $^1$H NMR and GPC analysis in order to evaluate the content. BHET:PET oligomer=93.0:7.0 w/w.

Example 18

Use of 10 mol % in situ generated salt organocatalyst DBU-BA (1:8 m/m) salt. To a 25 ml Schlenk tube containing PET flakes (0.48 g, 2.5 mmol) was charged a mixture of EG (2.49 g, 40 mmol), DBU (38 mg, 0.25 mmol), and BA (247 mg, 2.02 mmol). The tube was immersed in an oil bath and heated with stirring at 190° C. The slurry turned into a clear and homogeneous liquid in 324 minutes. Aliquots of the crude product were taken for $^1$H NMR and GPC analysis in order to evaluate the content. BHET:PET oligomer=91.7:8.2 w/w.

Example 19

Use of 10 mol % in situ generated salt organocatalyst DBU-Phenol (1:8 m/m) salt. To a 25 ml Schlenk tube containing PET flakes (0.48 g, 2.5 mmol) was charged a mixture of EG (2.50 g, 40 mmol), DBU (38 mg, 0.25 mmol), and phenol (192 mg, 2.04 mmol). The tube was immersed in an oil bath and heated with stirring at 190° C. The slurry turned into a clear and homogeneous liquid in 11 minutes. Aliquots of the crude product were taken for $^1$H NMR and GPC analysis in order to evaluate the content. BHET:PET oligomer=96.5:3.5 w/w.

Example 20

Use of 5 mol % of DBU. To a 25 ml Schlenk tube containing PET flakes (0.48 g, 2.5 mmol) was charged a mixture of EG (2.48 g, 40 mmol) and DBU (19 mg, 0.125 mmol). The tube was immersed in an oil bath and heated with stirring at 190° C. The slurry turned into a clear and homogeneous liquid in 22 minutes. Aliquots of the crude product were taken for $^1$H NMR and GPC analysis in order to evaluate the content. BHET:PET oligomer=94.6:5.4 w/w.

DBU-Catalyzed Depolymerization of PET Using Other Alcohols.

Example 21

16 mole equivalents of 1,3-Propanediol (PD). To a 25 ml Schlenk tube containing PET flakes (0.48 g, 2.5 mmol) was charged a mixture of PD (3.06 g, 40 mmol) and DBU (38 mg, 0.25 mmol). The tube was immersed in an oil bath and heated with stirring at 190° C. The slurry turned into a clear and homogeneous liquid in 15 minutes. Aliquots of the crude product were taken for $^1$H NMR and GPC analysis in order to evaluate the content. BHPT:PET oligomer=93.9:6.3 w/w.

Example 22

16 molar equivalents of 1,6-Hexanediol (HD). To a 25 ml Schlenk tube containing PET flakes (0.48 g, 2.5 mmol) was charged a mixture of HD (4.74 g, 40 mmol) and DBU (38 mg, 0.25 mmol). The tube was immersed in an oil bath and heated with stirring at 190° C. The slurry turned into a clear and homogeneous liquid in 90 minutes. Aliquots of the crude product were taken for $^1$H NMR and GPC analysis in order to evaluate the content. BHHT:PET oligomer=91.6:8.4 w/w.

Example 23

16 molar equivalents of benzyl alcohol (BzOH). To a 25 ml Schlenk tube containing PET flakes (0.48 g, 2.5 mmol) was charged a mixture of benzyl alcohol (4.29 g, 40 mmol) and DBU (38 mg, 0.25 mmol). The tube was immersed in an oil bath and heated with stirring at 190° C. The slurry turned into a clear and homogeneous liquid in 600 minutes. Aliquots of the crude product were taken for $^1$H NMR and GPC analysis in order to evaluate the content. The product contained no PET oligomer (0%). The depolymerization reaction has an equilibrium converting the monomer into the dimer/trimer when a glycol (diol) is used because the hydroxyl groups of the glycolyzed product can also serve as a nucleophile (see Scheme 1 below).

clear and homogeneous liquid in 80 minutes. Aliquots of the crude product were taken for $^1$H NMR and GPC analysis in order to evaluate the content. The product contained no PET oligomer (0%).

Example. 25

8 molar equivalents of 1-octanol. To a 25 ml Schlenk tube containing PET flakes (0.48 g, 2.5 mmol) was charged a mixture of 1-octanol (2.62 g, 20 mmol) and DBU (19 mg, 0.125 mmol). The tube was immersed in an oil bath and heated with stirring at 190° C. The slurry turned into a clear and homogeneous liquid in 65 minutes. Aliquots of the crude product were taken for $^1$H NMR and GPC analysis in order to evaluate the content. The product contained no PET oligomer (0%).

COMPARATIVE EXAMPLES

TBD Catalyzed Glycolysis of PET by EG

Comparative Example 1

Glycolysis of PET by EG using 10 mol % of 1,5,7-Triazabicyclo[4.4.0]dec-5-ene (TBD). To a 25 ml Schlenk tube containing PET flakes (0.96 g, 5.0 mmol) was charged a mixture of EG (4.97 g, 40 mmol) and TBD (70 mg, 0.5 mmol). The tube was immersed in an oil bath and heated with stirring at 190° C. The slurry turned into a clear and homogeneous liquid in 8 minutes. Aliquots of the crude product were taken for $^1$H NMR and GPC analysis in order to evaluate the content. BHET:PET oligomer=94.9:5.1 w/w.

Comparative Example 2

Glycolysis of PET by EG using 5 mol % TBD. To a 25 ml Schlenk tube containing PET flakes (0.48 g, 2.5 mmol) was charged a mixture of EG (2.48 g, 40 mmol) and TBD (35 mg, 0.25 mmol). The tube was immersed in an oil bath and heated with stirring at 190° C. The slurry turned into a clear and

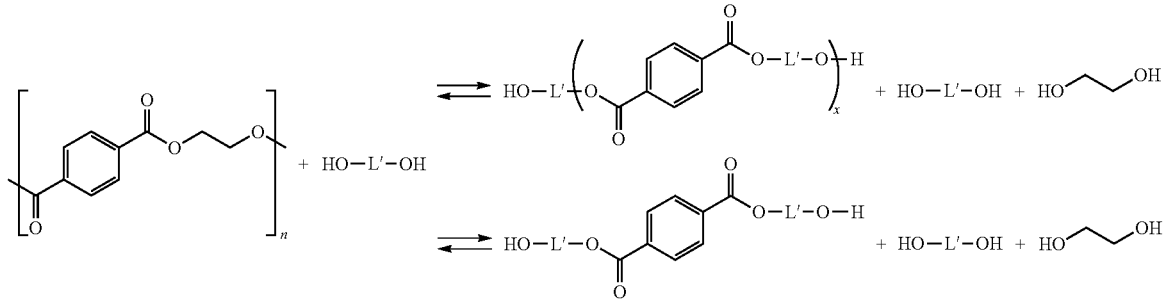

Scheme 1.

However, there is no equilibrium when a mono-alcohol is used. As a result no PET oligomer was observed in the product of PET depolymerization using mono-alcohols.

Example 24

16 molar equivalents of 1-octanol (OD). To a 25 ml Schlenk tube containing PET flakes (0.48 g, 2.5 mmol) was charged a mixture of 1-octanol (5.18 g, 40 mmol) and DBU (38 mg, 0.25 mmol). The tube was immersed in an oil bath and heated with stirring at 190° C. The slurry turned into a homogeneous liquid in 10 minutes. Aliquots of the crude product were taken for $^1$H NMR and GPC analysis in order to evaluate the content. BHET:PET oligomer=95.2:4.8 w/w.

Glycolysis of PET by EG Using No Catalyst

Comparative Example 3

Glycolysis of PET by EG using no base catalyst. To a 25 ml Schlenk tube containing PET flakes (0.48 g, 2.5 mmol) was charged EG (2.48 g, 40 mmol). The tube was immersed in an oil bath and heated with stirring at 190° C. The slurry turned into a clear and homogeneous liquid in 2400 minutes. Aliquots of the crude product were taken for $^1$H NMR and GPC analysis in order to evaluate the content. BHET:PET oligomer=90.6:9.4 w/w.

Glycolysis of PET by EG Catalyzed by Other Non-Amidine Bases: DMAP, DABCO, N-Methylimidazole, N,N-Dimethylaniline

Comparative Example 4

Glycolysis of PET by EG using 10 mol % of 4-(N,N-dimethylamino)pyridine (DMAP). To a 25 ml Schlenk tube containing PET flakes (0.96 g, 5.0 mmol) was charged a mixture of EG (4.97 g, 80 mmol) and DMAP (61 mg, 0.5 mmol). The tube was immersed in an oil bath and heated with stirring at 190° C. The slurry turned into a clear and homogeneous liquid in 100 minutes. Aliquots of the crude product were taken for $^1$H NMR and GPC analysis in order to evaluate the content. BHET:PET oligomer=93.6:6.4 w/w.

Comparative Example 5

Glycolysis of PET by EG using 10 mol % of 1,4-diazabicyclo[2.2.2]octane (DABCO). To a 25 ml Schlenk tube containing PET flakes (0.96 g, 5.0 mmol) was charged a mixture of EG (4.97 g, 80 mmol) and DABCO (57 mg, 0.51 mmol). The tube was immersed in an oil bath and heated with stirring at 190° C. The slurry turned into a clear and homogeneous liquid in 120 minutes. Aliquots of the crude product were taken for $^1$H NMR and GPC analysis in order to evaluate the content. BHET:PET oligomer=93.1:6.9 w/w.

Comparative Example 6

Glycolysis of PET by EG using 10 mol % of N-methylimidazole (NMI). To a 25 ml Schlenk tube containing PET flakes (0.96 g, 5.0 mmol) was charged a mixture of EG (4.97 g, 80 mmol) and NMI (43 mg, 0.5 mmol). The tube was immersed in an oil bath and heated with stirring at 190° C. The slurry turned into a clear and homogeneous liquid in 300 minutes. Aliquots of the crude product were taken for $^1$H NMR and GPC analysis in order to evaluate the content. BHET:PET oligomer=92.6:7.4 w/w.

Comparative Example 7

Glycolysis of PET by EG using 10 mol % of N,N-dimethylaniline (DMA). To a 25 ml Schlenk tube containing PET flakes (0.96 g, 5.0 mmol) was charged a mixture of EG (4.98 g, 80 mmol) and N,N-dimethylaniline (62 mg, 0.5 mmol). The tube was immersed in an oil bath and heated with stirring at 190° C. The slurry turned into a clear and homogeneous liquid in 2755 minutes. Aliquots of the crude product were taken for $^1$H NMR and GPC analysis in order to evaluate the content. BHET:PET oligomer=92.4:7.6 w/w.

Exposure of Base to Air

Comparative Example 8

Use of 10 mol % TBD exposed to the air for 24 hours. TBD (35 mg, 0.25 mmol) was placed in a 5 mL glass vial and the vial was left on a bench for 24 hours without the lid. EG (2.49 g, 40 mmol) was added to the vial and the mixture was charged to a 25 ml Schlenk tube containing PET flakes (0.48 g, 2.5 mmol). The tube was immersed in an oil bath and heated with stirring at 190° C. The slurry turned into a clear and homogeneous liquid in 50 minutes. Aliquots of the crude product were taken for $^1$H NMR and GPC analysis in order to evaluate the content. BHET:PET oligomer=93.9:6.1 w/w.

Base Concentration Dependence

Comparative Example 9

Use of 5 mol % TBD. To a 25 ml Schlenk tube containing PET flakes (0.48 g, 2.5 mmol) was charged a mixture of EG (2.49 g, 40 mmol) and TBD (17 mg, 0.125 mmol). The tube was immersed in an oil bath and heated with stirring at 190° C. The slurry turned into a clear and homogeneous liquid in 45 minutes. Aliquots of the crude product were taken for $^1$H NMR and GPC analysis in order to evaluate the content. BHET:PET oligomer=94.0:6.0 w/w.

Comparative Example 10

Use of 5 mol % of DMAP. To a 25 ml Schlenk tube containing PET flakes (0.48 g, 2.5 mmol) was charged a mixture of EG (2.50 g, 40 mmol) and DMAP (15 mg, 0.125 mmol). The tube was immersed in an oil bath and heated with stirring at 190° C. The slurry turned into a clear and homogeneous liquid in 90 minutes. Aliquots of the crude product were taken for $^1$H NMR and GPC analysis in order to evaluate the content. BHET:PET oligomer=93.7:6.3 w/w.

TBD-Catalyzed Glycolysis of PET by 1,3-Propanediol, 1,6-Hexanediol, and 1-Octanol

Comparative Example 11

1,3-Propanediol (PD). To a 25 ml Schlenk tube containing PET flakes (0.48 g, 2.5 mmol) was charged a mixture of PD (3.06 g, 40 mmol) and TBD (35 mg, 0.25 mmol). The tube was immersed in an oil bath and heated with stirring at 190° C. The slurry turned into a clear and homogeneous liquid in 20 minutes. Aliquots of the crude product were taken for $^1$H NMR and GPC analysis in order to evaluate the content. BHPT:PET oligomer=92.3:7.7 w/w.

Comparative Example 12

1,6-Hexanediol (HD). To a 25 ml Schlenk tube containing PET flakes (0.48 g, 2.5 mmol) was charged a mixture of HD (4.75 g, 40 mmol) and TBD (35 mg, 0.25 mmol). The tube was immersed in an oil bath and heated with stirring at 190° C. The slurry turned into a clear and homogeneous liquid in 26 minutes. Aliquots of the crude product were taken for $^1$H NMR and GPC analysis in order to evaluate the content. BHHT:PET oligomer=92.1:7.9 w/w.

Comparative Example 13

Use of 5 mol % of TBD and 1-octanol. To a 25 ml Schlenk tube containing PET flakes (0.48 g, 2.5 mmol) was charged a mixture of 1-octanol (2.62 g, 20 mmol) and TBD (17 mg, 0.125 mmol). The tube was immersed in an oil bath and heated with stirring at 190° C. The slurry turned into a clear and homogeneous liquid in 4.5 minutes. Aliquots of the crude product were taken for $^1$H NMR and GPC analysis in order to evaluate the content. The product contained no PET oligomer (0%).

Comparative Example 14

Use of 5 mol % of DMAP and 1-octanol. To a 25 ml Schlenk tube containing PET flakes (0.48 g, 2.5 mmol) was charged a mixture of 1-octanol (2.61 g, 20 mmol) and DMAP (15 mg, 0.125 mmol). The tube was immersed in an oil bath and heated with stirring at 190° C. The slurry turned into a clear and homogeneous liquid in 1600 minutes. Aliquots of the crude product were taken for ¹H NMR and GPC analysis in order to evaluate the content. The product contained no PET oligomer (0%).

Effect of Process Temperature.

Figure 2:
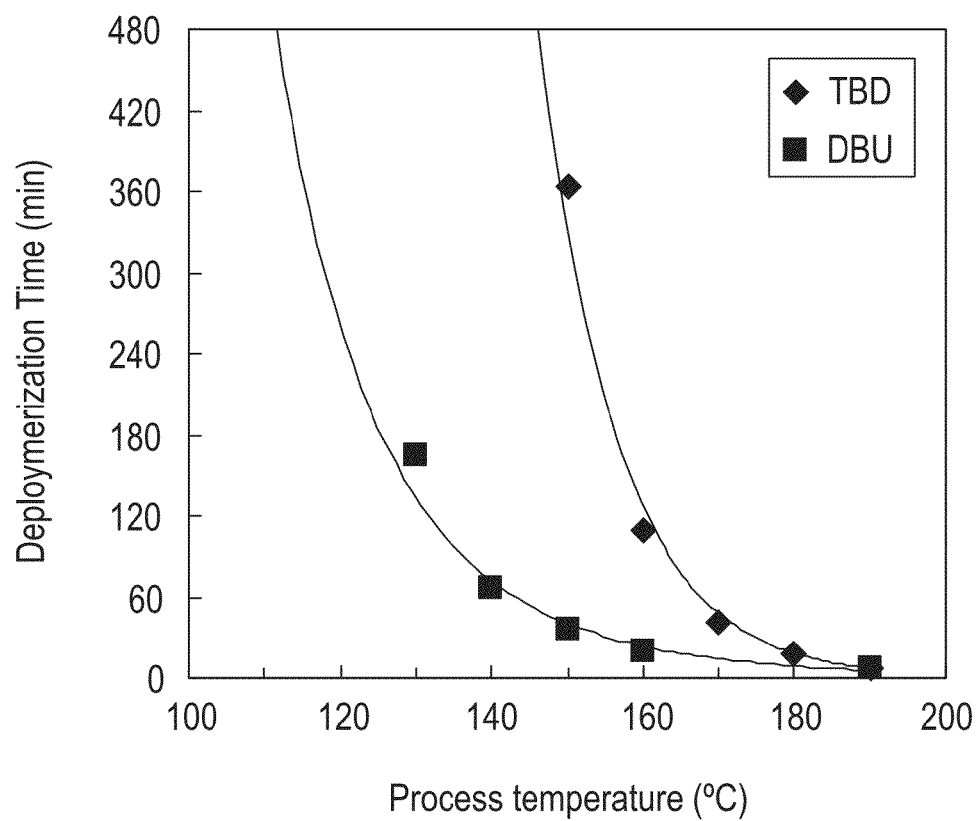
FIG. 2 is a graph comparing degradation times (i.e., depolymerization time) as a function of process temperature for the glycolysis of PET (0.48 g) with EG (2.48 g) when catalyzed by cyclic amidine 1,8-diazabicyclo(5.4.0)undec-7-ene (DBU) and cyclic guanidine triazabicyclo[4.4.0]dec-5-ene TBD (10 mol % relative to PET).

FIG. 2 is a graph comparing depolymerization time (degradation time in the graph) versus process temperature for the EG glycolysis of post-consumer PET catalyzed by DBU and TBD alone (i.e., not in the form of a salt), other conditions being identical. The depolymerization completed faster for DBU than TBD at process temperatures of 120° C. to 189° C., and particularly 130° C. to 180° C. The depolymerization times converged for the two catalysts at about 190° C.

Effect of Catalyst Loading.

Figure 3:
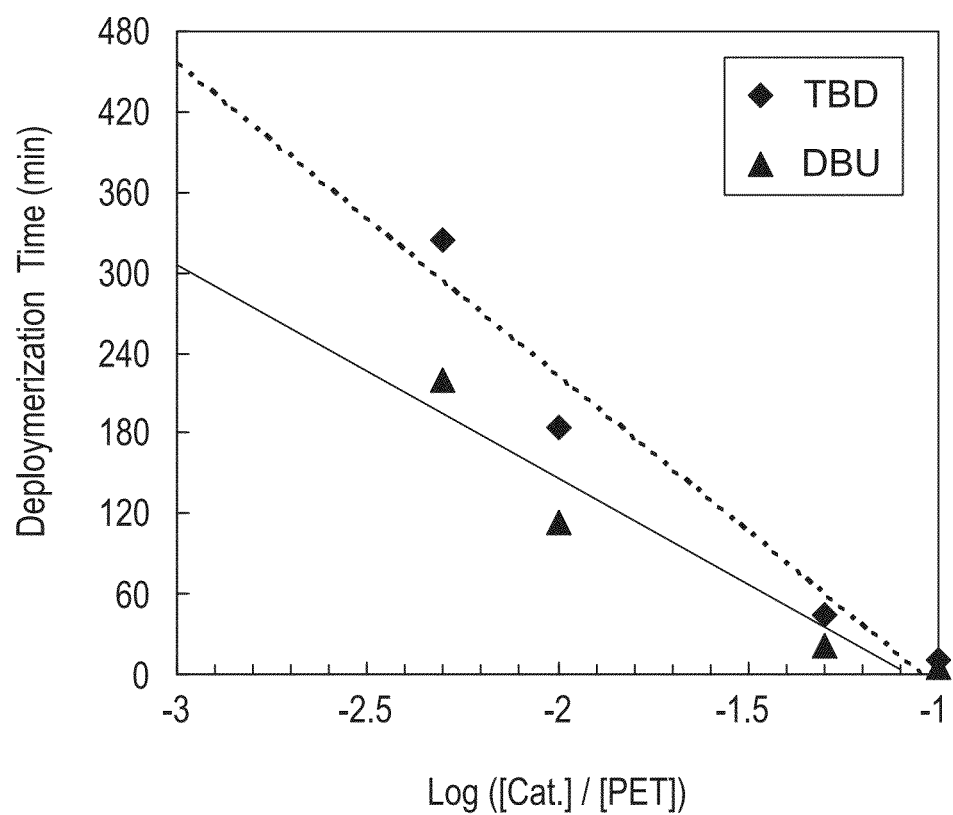
FIG. 3 is a graph comparing degradation times (depolymerization time) as a function of catalyst loading ([Cat.]/[PET]) for the glycolysis of PET (0.48 g) with EG (2.48 g) at 190° C. when catalyzed by DBU and TBD.

FIG. 3 is a graph comparing the depolymerization time (degradation time in the graph) versus catalyst loading for the EG glycolysis of post-consumer PET catalyzed by DBU and TBD alone, other conditions being equivalent. At each catalyst loading below 10 mole %, the depolymerization time was less for DBU than TBD. The depolymerization times converged for the two catalysts at a catalyst loading of about 10 mol %.

Effect of EG Content on PET Oligomer.

Figure 4:
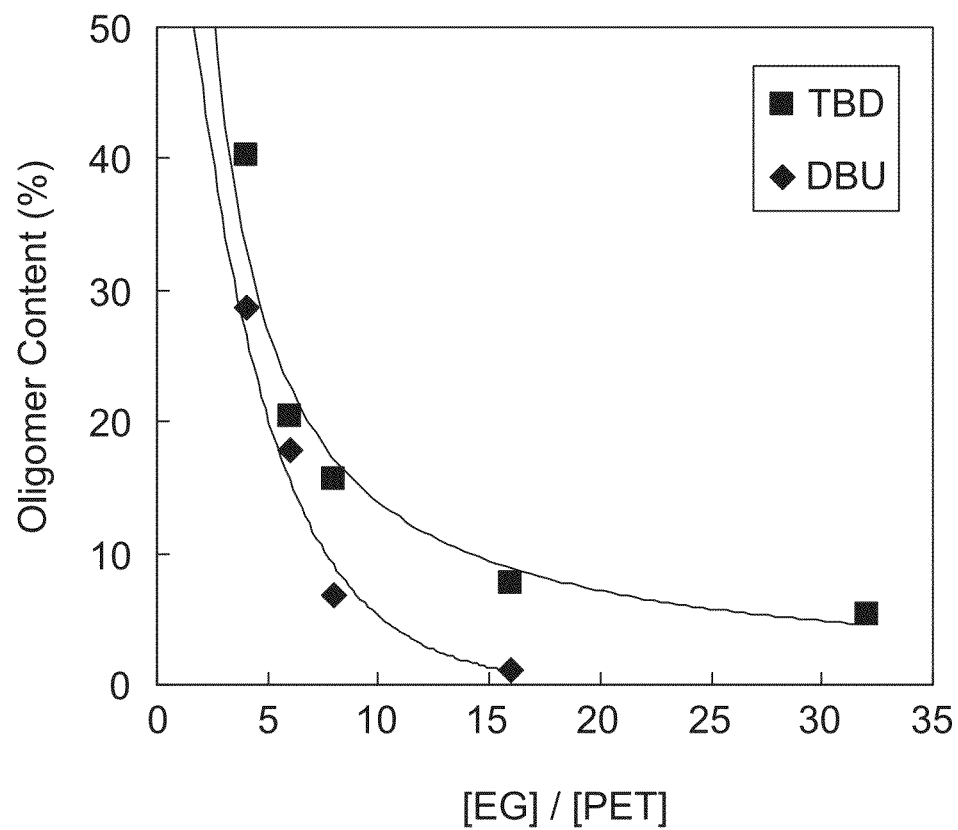
FIG. 4 is graph comparing PET oligomer content in the crude product as a function of EG loading ([EG]/[PET]) for the glycolysis of PET (0.48 g) with EG at 190° C. when catalyzed by DBU and TBD (10 mol %). The oligomer content is less for DBU compared to TBD at each EG loading of 4 to 16 molar equivalents. For oligomer content less than 10 wt. %, an EG loading of about 8 equivalents or more can be used in the DBU catalyzed depolymerization, whereas EG loadings of 16 equivalents or more are required using TBD.

FIG. 4 is a graph comparing the PET oligomer content in the crude product as a function of EG concentration (4, 6, 8 and 16 molar equivalents compared to moles of PET repeat unit) used in the EG glycolysis of post-consumer PET catalyzed by DBU and TBD alone, other conditions being equivalent. The DBU-catalyzed glycolysis contained fewer amounts of oligomers than the TBD-catalyzed glycolysis. This is unexpected because typically the catalytic activity of these superbases (DBU, DBN, and TBD) correlates with basicity in ring-opening polymerizations. The pKa values of TBD and DBU are 26.03 and 24.34, respectively, in acetonitrile. It is another advantage of the disclosed methods that using about 8 molar equivalents of ethylene glycol relative to the PET repeat unit, the DBU-catalyzed glycolysis can produce the terephthalate product containing more than 90 wt. % BHET, and less than 10 wt. % terephthalate oligomers based on a total weight of the terephthalate reaction product. This is not possible using TBD and other catalysts.

As comparative examples, the EG glycolysis of PET was conducted using different nitrogen bases (Table 2). The catalyst activity generally conformed to the catalyst basicity in the EG glycolysis, except for TBD, which produced PET oligomer in an amount similar to dimethylaminopyridine (DMAP), despite the large difference in pKa between these bases.

TABLE 2

| Examplee | Catalyst | Feed (mol %) | pKa (acetonitrile) | pKa (water) | Rxn. Time (min) | Oligomer[c] (wt. %) |
|---|---|---|---|---|---|---|
| Ex. 1 | DBU[a] | 10 | 24.34 | 11.9 | 6.5 | 1.1 |
| Ex. 3 | DBN[a] | 10 | NA | 11.0 | 7 | 1.5 |
| CEx. 1 | TBD[a] | 10 | 26.03 | NA | 8 | 5.1 |
| CEx. 4 | DMAP[a] | 10 | 17.95 | 9.7 | 100 | 6.4 |
| CEx. 5 | DABCO[a] | 10 | NA | 8.2 | 120 | 6.9 |
| CEx. 6 | NMI[a] | 10 | NA | 7.4 | 300 | 7.4 |
| CEx. 7 | DMA[a] | 10 | 11.43 | 5.07 | 2755 | 7.6 |
| Ex. 12 | PS-DBU[b] | 10 | NA | NA | 180 | 6.6 |
| Ex. 20 | DBU[b] | 5 | 24.34 | 11.9 | 22 | 5.4 |
| CEx. 9 | TBD[b] | 5 | 26.03 | NA | 45 | 6.0 |
| CEx. 10 | DMAP[b] | 5 | 17.95 | 9.7 | 90 | 6.3 |
| CEx. 3 | No catalyst[b] | NA | NA | NA | 2400 | 9.4 |

[a]Reaction was conducted using PET (0.96 g) and EG (4.98 g) at 190° C.
[b]Reaction was conducted using PET (0.48 g) and EG (2.48 g) at 190° C.
[c]Determined by GPC.

Computational studies using methanolysis of dimethyl terephthalate (DMT) catalyzed by TBD revealed that EG plays a role not only as a reactant but also as a catalyst to activate carbonyl groups of PET through hydrogen bonding (H-bonding) under the typical reaction conditions where excess EG is loaded. FIG. 5 is a graph showing calculated energies and molecular models of the reactants, initial reactant complex, transition state, and intermediate product in the methanolysis reaction with EG present. The modeling results indicate EG activates the carbonyl groups of PET through hydrogen bonding (H-bonding). FIG. 6 is a graph showing the calculated energies and molecular models of the reactants, initial reactant complex, transition state, and intermediate product in the methanolysis reaction of DMT without EG present. The activation of DMT by EG contributes to lowering the energy barrier at the rate determining step more than bi-functional TBD alone (11.5 (FIG. 5) vs. 15.9 kcal/mol (FIG. 6)).

The rate of the EG glycolysis reaction is significantly dependent on the manner in which the catalyst activates the hydroxyl groups of EG. TBD activates the hydroxyl group of EG through double H-bonds. One of the H-bonds between a hydrogen atom of TBD and an oxygen atom of EG somewhat mitigates the nucleophilicity of EG, as shown in the following Scheme 2.

Scheme 2.

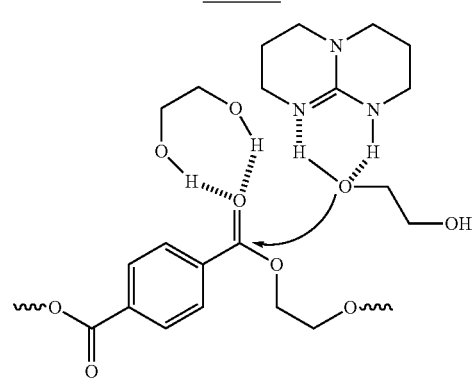

By comparison, the non-bi-functional DBU simply activates the hydroxyl group, as shown below in Scheme 3.

Scheme 3.

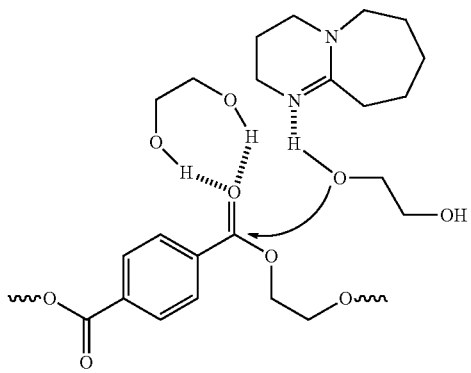

Thus, although DBU is less basic than TBD, DBU exhibits higher catalytic activity than TBD in EG glycolysis of PET.

The extent of the contribution by diols to the activation of PET gradually declines as the number of methylene units between the two hydroxyl groups increases, believed to be due to steric hindrance and a distorted H-bond configuration around the carbonyl oxygen. Table 3 summarizes PET depolymerizations performed with different alcohols. The results indicate that the H-bond activation of PET by mono-alcohols that have a bulky moiety and high boiling point is also quite small compared to EG. Moreover, the glycolysis reaction with TBD shows higher efficiency with 1,6-hexanediol and 1-octanol than any other catalyst including DBU, attributed to bi-functional TBD providing activation of the carbonyl group of PET. Thus, in the absence of major activation of PET by diols, the catalytic activity in the depolymerization of PET is more in accordance with the basicity of the catalyst. Under these conditions, the advantages of bi-functional activation by TBD become more prominent.

TABLE 3

| Example[a] | Reagent | Feed (equiv.) | Catalyst | Feed (mol %) | Rxn. Time (min) | Oligomer[b] (wt. %) |
|---|---|---|---|---|---|---|
| Ex. 21 | 1,3-Propanediol | 16 | DBU | 10 | 15 | 6.3 |
| CEx. 11 | 1,3-Propanediol | 16 | TBD | 10 | 20 | 7.7 |
| Ex. 22 | 1,6-Hexanediol | 16 | DBU | 10 | 90 | 8.4 |
| CEx. 12 | 1,6-Hexanediol | 16 | TBD | 10 | 26 | 7.9 |
| Ex. 23 | Benzyl alcohol | 16 | DBU | 10 | 600 | NA |
| Ex. 24 | 1-Octanol | 16 | DBU | 10 | 80 | NA |
| Ex. 25 | 1-Octanol | 8 | DBU | 5 | 65 | NA |
| CEx. 13 | 1-Octanol | 8 | TBD | 5 | 4.5 | NA |
| CEx. 14 | 1-Octanol | 8 | DMAP | 5 | 1600 | NA |

[a]Reactions were conducted at 190° C. using PET (0.48 g).
[b]Determined by GPC.

The efficiency of salt organocatalysts in the PET glycolysis reaction with EG is also subject to the basicity of the base catalyst as well as the acidity of the acid component of the salts (Table 4).

TABLE 4

| Example[a] | Catalyst | DBU:Acid (molar ratio) | pKa of acid (water) | Rxn. Time (min) | Oligomer[e] (wt. %) |
|---|---|---|---|---|---|
| Ex. 3 | DBU-Phenol[b] | 1:1 | 9.95 | 9 | 3.3 |
| Ex. 19 | DBU-Phenol[c] | 1:8 | 9.95 | 11 | 3.5 |
| Ex. 9 | DBU-PFA[c] | 1:0.5 | NA | 7 | 4.7 |
| Ex. 4 | DBU-BA[b] | 1:1 | 4.2 | 40 | 7.2 |
| Ex. 17 | DBU-BA[c] | 1:2 | 4.2 | 150 | 7.0 |
| Ex. 18 | DBU-BA[c] | 1:8 | 4.2 | 324 | 8.2 |
| Ex. 11 | DBU-pTSA[c,d] | 1:1 | −2.4 | 1120 | 8.1 |
| Ex. 13 | (PS-DBU)-BA[c] | 1:1 | NA | 360 | 7.4 |

[a]Reaction was conducted at 190° C. using PET (0.48 g), EG (2.48 g) and catalyst (10 mol %).
[b]Pre-formed.
[c]In situ formation.
[d]Reaction was conducted with PET (0.96 g), EG (4.98 g).
[e]Determined by GPC.

The salt organocatalysts formed with oxo acids such as benzoic acid (BA) and p-toluene sulfonic acid (pTSA) are more likely to exist as an ion pair of a conjugate acid and a conjugate base rather than as dissociated ions or a pair of an acid and a base, according to a computational result (FIG. 7), which was supported by experimental findings using NMR techniques (FIG. 8). This result is consistent with the fact that a weaker acid can be a stronger conjugate base. Salt organocatalysts comprising more than 1 equivalent of an acid component showed lower catalytic efficiency and had longer reaction times than the equimolar salts.

Table 5 summarizes PET depolymerizations using catalysts exposed to air. The salt organocatalyst, DBU-BA (1:1) can be used in a PET depolymerization after exposure to air for 24 hours while retaining much of the initial catalytic activity. In contrast, the other catalysts had significantly lower catalytic activity after exposure to air for 24 hours. Depolymerizations required 3 times the reaction time compared to the fresh catalysts (compare Table 5 with Tables 2 and 4).

TABLE 5

| Example[a] | Catalyst | Rxn. Time (min) | Oligomer[b] (wt. %) |
|---|---|---|---|
| Ex. 14 | DBU | 35 | 5.1 |
| Ex. 15 | DBU-BA (1:1) | 45 | 4.6 |
| Ex. 16 | DBU-Phenol (1:1) | 26 | 5.8 |
| CEx. 8 | TBD | 50 | 6.1 |

[a]Reaction was conducted at 190° C. using PET (0.48 g), EG (2.48 g) and catalyst (10 mol %).
[b]Determined by GPC.

Other commercially available post-consumer PET was tested, including bottles, colored bottles, and pellets (Aldrich, Eastman, and Polyscience). Increasing crystallinity, increasing size of the PET flakes (surface area in contact with glycol), and increasing thickness of PET flakes slow the glycolysis reaction time with EG. DBU and TBD are affected in the same direction and degree by these changes. Dyes and pigments also slowed the depolymerization time. Without being bound by theory, most dyes and pigments are acidic, which mitigates the catalytic activity of the bases DBU and TBD.

Example 26

PET Glycolysis 200 Gram PET Scale

A 2 liter 3-neck round bottom flask was equipped with: 1) a mechanical overhead stirrer, 2) a temperature controlled heating mantle, 3) a thermocouple thermometer, 4) an inlet for dry nitrogen gas. The flask was charged with 200 grams of clean PET flake (1.04 mol), 1000 grams of ethylene glycol (16.11 mol), and DBU (1.58 grams, 0.01 mol), as shown in a photograph of FIG. 9. The flask was flushed with nitrogen, and heated under a nitrogen atmosphere for 6 hours at 190° C. to 195° C. At this point the reaction progressed from a suspension to a clear pale yellow solution containing BHET, as shown in the photograph of FIG. 10. The reaction was cooled slowly over one hour to ambient temperature to allow BHET crystallization to occur, and was then stirred in an ice-water cooling bath for 2 hours. The resulting product was vacuum filtered through a coarse glass fritted funnel (pore size 25-50 microns), as shown in the photograph of FIG. 11 to yield a cream colored solid (209 grams, 79%).

Example 27

Use of 10 mol % In Situ Generated Salt Organocatalyst DBU-TA (2:1 m/m) Salt Organocatalyst, 2.5 mmol PET To a 25 ml Schlenk tube containing PET flakes (0.48 g, 2.5 mmol) was charged a mixture of EG (2.48 g, 40 mmol), DBU (38 mg, 0.25 mmol), and terephthalic acid (TA) (21 mg, 0.126 mmol). The tube was immersed in an oil bath and heated with stirring at 190° C. The slurry turned into a clear and homogeneous liquid in 65 minutes. Aliquots of the crude product were taken for $^1$H NMR and GPC analysis in order to evaluate the content. BHET:PET oligomer=92.1:7.9 w/w.

Example 28

Use of 10 mol % Pre-Formed Salt Organocatalyst SC-3 (DBU-TA (2:1 m/m), 2.5 mmol PET Preparation of salt organocatalyst SC-3 (DBU-TA, 2:1 m/m) with DBU and terephthalic acid. A DMF solution (10 mL) of DBU (3.24 g, 21.3 mmol) was added to a 50 mL flask containing DMF (25 mL) and terephthalic acid (TA) (1.67 g, 10.1 mmol) upon heating at 70° C. under nitrogen atmosphere. The solution was heated for 1 hour with stirring, cooled down to ambient temperature and left at rest overnight. The crystallized product was then filtered, washed with THF several times, and dried under vacuum (4.67 g, 98%).

Depolymerization of PET using SC-3. To a 25 ml Schlenk tube containing PET flakes (0.48 g, 5.0 mmol) was charged a mixture of EG (2.48 g, 40 mmol), and pre-formed salt organocatalysts SC-3 (59 mg, 0.125 mmol). The tube was immersed in an oil bath and heated with stirring at 190° C. The slurry turned into a clear and homogeneous liquid in 70 minutes. Aliquots of the crude product were taken for $^1$H NMR and GPC analysis in order to evaluate the content. BHET:PET oligomer=92.1:7.9 w/w.

The above examples demonstrate that the reaction time and/or the reaction temperature of the depolymerization of post-consumer PET can be significantly lowered using an amidine organocatalyst or an amidine salt organocatalyst and a glycol comprising 2 to 5 carbons. The examples also demonstrate that the glycol itself is a co-catalyst, ethylene glycol being particularly advantaged for steric reasons. Other observations indicate that the mole ratio of amidine organocatalyst to PET repeat unit can also be significantly lowered compared to TBD for depolymerizations conducted with a linear glycol having 2 to 5 carbons, particularly ethylene glycol. In view of these results, the disclosed methods potentially allow for significant conservation of materials and energy used in large scale recycling processes for post-consumer PET and post-consumer PBT.

Comparison Examples 29 to 34

Glycolysis of Dimethyl Terephthalate (DMT) at Ambient Temperature with DBU and TBD Materials.

DMT and Amberlyst-15 was purchased from Sigma-Aldrich and used as received.

To a 5 ml sample tube containing DMT (0.48 g, 2.5 mmol) was charged predetermined amounts of EG and a catalyst (DBU or TBD, 0.125 mmol, 0.05 eq.). Three levels of EG were used with each catalyst: 2.84 molar equivalents, 8 molar equivalents, and 16 molar equivalents of EG relative to moles of DMT. After the mixture was stirred for 24 hours, THF (8 mL) and Amberlyst-15 (150 mg) were added to the mixture to quench the reaction and allow the slurry to become homogeneous. Aliquots of the solution were taken for $^1$H NMR and GPC analysis in order to evaluate the conversion and content. FIG. 12 shows a typical GPC curve of the crude product. Peak labeled A corresponds to oligomers, peak labeled B corresponds to BHET, peak labeled C corresponds to 2-hydroxyethyl methyl terephthalate (HEMT), and peaks labeled D correspond to EG and DMT. HEMT is the intermediate in glycolysis of DMT and has the following structure:

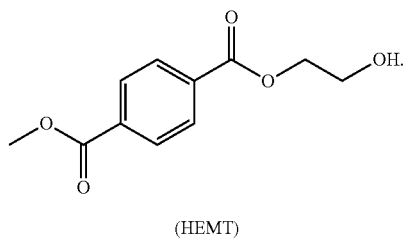 [SMILES: COC(=O)c1ccc(C(=O)OCCO)cc1]

(HEMT)

The GPC results are summarized in Table 6 below.

TABLE 6

| Example | Catalyst | EG | Conv. (%)$^a$ | Oligomer$^b$ (A) (wt. %) | BHET$^b$ (B) (wt. %) | HEMT$^b$ (C) (wt. %) | EG + DMT$^b$ (D) (wt. %) |
|---|---|---|---|---|---|---|---|
| CEx. 29 | DBU | 0.44 g (7.1 mmol, 2.84 eq.) | 15 | 0.2 | 13.0 | 1.8 | 85.0 |
| CEx. 30 | DBU | 1.26 g (20 mmol, 8 eq.) | 47 | 0.7 | 33.3 | 4.4 | 61.6 |

TABLE 6-continued

| Example | Catalyst | EG | Conv. (%)[a] | Oligomer[b] (A) (wt. %) | BHET[b] (B) (wt. %) | HEMT[b] (C) (wt. %) | EG + DMT[b] (D) (wt. %) |
|---|---|---|---|---|---|---|---|
| CEx. 31 | DBU | 2.49 g (40 mmol, 16 eq.) | 83 | 1.1 | 35.2 | 8.5 | 55.2 |
| CEx. 32 | TBD | 0.44 g (7.1 mmol, 2.84 eq.) | 32 | 2.2 | 15.0 | 27.2 | 55.6 |
| CEx. 33 | TBD | 1.26 g (20 mmol, 8 eq.) | 51 | 1.6 | 25.9 | 22.1 | 50.4 |
| CEx. 34 | TBD | 2.49 g (40 mmol, 16 eq.) | 94 | 1.1 | 34.3 | 13.7 | 50.9 |

[a]Conversions were obtained from $^1$H NMR.
[b]determined by GPC.

The results in Table 6 indicate that the DBU catalyzed glycolysis reactions of DMT at ambient temperature are less reactive compared to the TBD catalyzed reactions at each EG level, as evidenced by the lower % Conversion and higher EG+DMT wt. %. The results in Table 6 also indicate that the DBU catalyzed reactions are more selective compared to the TBD catalyzed reactions at each EG level, as evidenced by the ratio of peak B to peak A, and ratio of peak B to peak C. As shown in Table 6, the TBD and DBU catalyzed reactions at ambient temperature produce about the same amount of BHET at the lowest EG level (compare BHET content in Examples 29 and 32) and at the highest EG level (compare BHET content in Examples 31 and 34). At 8 equivalents EG (Examples 30 and 33), the DBU catalyzed reaction produced more BHET compared to the TBD catalyzed reaction (33.3 wt. % vs. 25.9 wt. %, respectively). This advantage was offset by the DBU reaction also having a lower percent conversion (47% vs 51% for TBD) and higher EG+DMT content (61.6 wt. % vs. 50.4 wt. % for TBD).

Example 35

Glycolysis of Poly(Butylene Terephthalate) (PBT) by 1,4-Butanediol (BD)

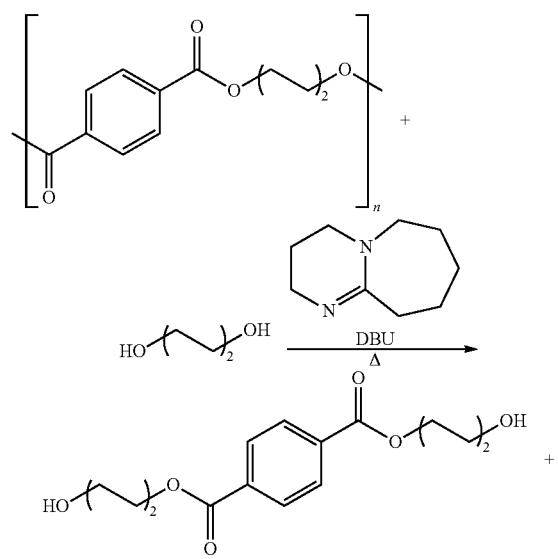

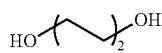

PBT pellet was purchased from Sigma-Aldrich, dissolved in 10% trifluoroacetic acid containing chloroform (100 ml), precipitated in methanol (1 L), and dried in vacuum at 50° C. overnight prior to use. 1,4-butanediol was purchased from Spectrum Chemical and used as received.

To a 50 ml sample tube containing PBT (0.55 g, 2.5 mmol) was charged 1,4-butanediol (3.63 g, 40 mmol) and DBU (38 mg, 0.125 mmol). The tube was immersed in an oil bath and heated with stirring at 190° C. for 1 hour. The slurry turned into a clear and homogeneous liquid in 30 minutes. Aliquots of the crude product were taken for $^1$H NMR and GPC analysis in order to evaluate the content. The reaction mixture was dissolved in chloroform (80 mL) and washed with water (100 mL). The organic layer was then stirred over MgSO$_4$, evaporated, and dried in vacuum to give the product bis(4-hydroxybutyl) terephthalate (BHBT) (0.70 g, 90%). BHBT: PBT oligomer=90.1:9.9 w/w.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A method, comprising:
   forming a reaction mixture comprising a terephthalate polyester, a glycol comprising 2 to 5 carbons, and an amidine organocatalyst; and
   heating the reaction mixture at a temperature of about 120° C. or more to depolymerize the terephthalate polyester, thereby forming a terephthalate reaction product comprising a monomeric dihydroxy terephthalate diester;
   wherein the terephthalate reaction product contains terephthalate oligomers in an amount less than the amount of terephthalate oligomers that would result from i) substituting the amidine organocatalyst with an equimolar amount of a guanidine catalyst and ii) depolymerizing the terephthalate polyester under otherwise identical reaction conditions.

2. The method of claim 1, wherein the glycol is present in an amount of about 4 to about 20 molar equivalents relative to total moles of terephthalate repeat unit present in the terephthalate polyester.

3. The method of claim 1, wherein the glycol is present in an amount of about 8 to about 16 molar equivalents relative to total moles of terephthalate repeat unit present in the terephthalate polyester.

4. The method of claim 1, wherein the terephthalate reaction product comprises 90 wt. % or more of monomeric dihydroxy terephthalate diester, based on total weight of the terephthalate reaction product.

5. The method of claim 1, wherein the glycol is a co-catalyst.

6. The method of claim 1, wherein the terephthalate polyester is post-consumer poly(ethylene terephthalate) (PET).

7. The method of claim 1, wherein the terephthalate polyester is post-consumer poly(butylene terephthalate) (PBT).

8. The method of claim 1, wherein the reaction mixture is heated at a temperature in the range of about 120° C. to about 190° C.

9. The method of claim 1, wherein the reaction mixture is heated at a temperature in the range of about 130° C. to about 180° C.

10. The method of claim 1, wherein the amidine catalyst is present in an amount of 0.001 to 0.1 molar equivalents relative to total moles of terephthalate repeat unit present in the terephthalate polyester.

11. The method of claim 1, wherein the glycol is selected from the group consisting of ethylene glycol, 1,3-propanediol, 1,4-butanediol, and 1,5-pentanediol.

12. The method of claim 1, wherein the terephthalate polyester is poly(ethylene terephthalate) (PET), the glycol is ethylene glycol, and the dihydroxy terephthalate diester is bis(2-hydroxyethyl)terephthalate (BHET).

13. The method of claim 1, wherein the terephthalate polyester is poly(butylene terephthalate) (PBT), the glycol is 1,4-butanediol, and the dihydroxy terephthalate diester is bis(4-hydroxybutyl)terephthalate (BHBT).

14. The method of claim 1, wherein the amidine catalyst is selected from the group consisting of 1,8-diazabicycloundec-7-ene (DBU), 1,5-diazabicyclo[4.3.0]non-5-ene (DBN), polymer supported DBU, polymer supported DBN, and combinations thereof.

15. The method of claim 1, wherein a chemical formula of the amidine organocatalyst does not contain any metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table.

16. The method of claim 1, wherein an organic acid is included in the reaction mixture before depolymerizing the terephthalate polyester.

17. The method of claim 16, wherein the organic acid is present in an amount of 0.1 to 10 molar equivalents relative to moles of the amidine base.

18. The method of claim 16, wherein the organic acid is terephthalic acid.

19. The method of claim 1, further comprising i) cooling the reaction mixture after the depolymerization and ii) isolating the dihydroxy terephthalate diester by direct filtration.

20. The method of claim 1, wherein the amidine organocatalyst is a pre-formed amidine salt organocatalyst comprising an amidine base and an organic acid.

21. A method, comprising:
   forming a reaction mixture comprising a terephthalate polyester, an amidine organocatalyst, and a glycol in an amount of about 8 to about 16 molar equivalents relative to total moles of terephthalate repeat unit present in the terephthalate polyester, the glycol comprising 2 to 5 carbons, wherein the glycol is a co-catalyst; and
   heating the reaction mixture at a temperature in the range of about 120° C. to about 210° C. to depolymerize the terephthalate polyester, thereby forming a terephthalate reaction product comprising a monomeric dihydroxy terephthalate diester in an amount of 90 wt. % or more based on a total weight of the terephthalate reaction product.

22. The method of claim 21, wherein an organic acid is included in the reaction mixture before depolymerizing the terephthalate polyester.

23. The method of claim 21, wherein the amidine organocatalyst is a pre-formed amidine salt organocatalyst comprising an amidine base and an organic acid.

24. The method of claim 21, wherein the glycol is present in an amount of about 8 to about 16 molar equivalents relative to the terephthalate repeat unit and the terephthalate reaction product contains less than about 10 wt. % of terephthalate oligomers based on a total weight of the terephthalate reaction product.

25. A method of preparing bis(2-hydroxyethyl)terephthalate (BHET), comprising:
   forming a reaction mixture comprising poly(ethylene terephthalate) (PET), ethylene glycol in an amount of 4 to about 20 molar equivalents relative to a PET repeat unit, and an amidine organocatalyst; and
   heating the reaction mixture at a temperature in the range of about 120° C. to about 210° C. to depolymerize the poly(ethylene terephthalate), thereby producing a terephthalate reaction product comprising bis(2-hydroxyethyl)terephthalate (BHET), wherein the BHET is present in an amount of 94 wt. % to 100 wt. % based on a total weight of the terephthalate reaction product.

26. The method of claim 25, wherein an organic acid is included in the reaction mixture before depolymerizing the poly(ethylene terephthalate), and the terephthalate reaction product comprises the BHET in an amount of 96 wt. % to 100 wt. % based on a total weight of the terephthalate reaction product.

27. The method of claim 25, wherein the amidine organocatalyst is a pre-formed amidine salt organocatalyst comprising an amidine base and an organic acid, and the terephthalate reaction product comprises the BHET in an amount of 96 wt. % to 100 wt. % based on a total weight of the terephthalate reaction product.

28. The method of claim 25, wherein the ethylene glycol is present in an amount of about 8 to about 16 molar equivalents relative to moles of the poly(ethylene terephthalate) (PET) repeat unit.

29. The method of claim 25, wherein the poly(ethylene terephthalate) is post-consumer poly(ethylene terephthalate).

30. A method of preparing bis(4-hydroxybutyl)terephthalate (BHBT), comprising:

forming a reaction mixture comprising poly(butylene terephthalate) (PBT), an amidine organocatalyst, and 4 to 20 molar equivalents of 1,4-butanediol relative to moles of poly(butylene terephthalate) repeat unit present in the PBT; and heating the reaction mixture at a temperature in the range of about 120° C. to about 210° C. to depolymerize the poly(butylene terephthalate), thereby forming a terephthalate reaction product comprising bis(4-hydroxybutyl)terephthalate (BHBT).

31. The method of claim 30, wherein an organic acid is included in the reaction mixture before depolymerizing the poly(butylene terephthalate).

32. The method of claim 30, wherein the amidine organocatalyst is a pre-formed amidine salt organocatalyst comprising an amidine base and an organic acid.

33. The method of claim 30, wherein the 1,4-butanediol is present in an amount of about 8 to about 16 molar equivalents relative to moles of the poly(butylene terephthalate) repeat unit and the terephthalate reaction product comprises 90 wt. % or more of bis(4-hydroxybutyl)terephthalate (BHBT) based on a total weight of the terephthalate reaction product.

34. The method of claim 30, wherein the poly(butylene terephthalate) is post-consumer poly(butylene terephthalate).

35. The method of claim 1, wherein the amidine organocatalyst is 1,8-diazabicycloundec-7-ene (DBU).

36. The method of claim 21, wherein the amidine organocatalyst is 1,8-diazabicycloundec-7-ene (DBU).

37. The method of claim 25, wherein the amidine organocatalyst is 1,8-diazabicycloundec-7-ene (DBU).

38. The method of claim 30, wherein the amidine organocatalyst is 1,8-diazabicycloundec-7-ene (DBU).

* * * * *